(12) United States Patent
McGrath et al.

(10) Patent No.: US 8,255,036 B2
(45) Date of Patent: Aug. 28, 2012

(54) OXYGEN-ENHANCED MAGNETIC RESONANCE IMAGING TECHNIQUE AND COMPARTMENTAL MODEL ALGORITHM

(75) Inventors: Deirdre McGrath, Manchester (GB); Geoffrey Parker, Manchester (GB)

(73) Assignee: The University of Manchester, Manchester (GB)

( * ) Notice: Subject to any disclaimer, the term of this patent is extended or adjusted under 35 U.S.C. 154(b) by 405 days.

(21) Appl. No.: 12/598,580

(22) PCT Filed: Apr. 18, 2008

(86) PCT No.: PCT/GB2008/001390
§ 371 (c)(1),
(2), (4) Date: Nov. 2, 2009

(87) PCT Pub. No.: WO2008/135712
PCT Pub. Date: Nov. 13, 2008

(65) Prior Publication Data
US 2010/0145186 A1    Jun. 10, 2010

(30) Foreign Application Priority Data
May 3, 2007  (GB) .................................. 0708567.3

(51) Int. Cl.
*A61B 5/00* (2006.01)
(52) U.S. Cl. ............. 600/416; 703/2; 600/410; 424/9.1; 436/173
(58) Field of Classification Search .................. 600/407, 600/410, 411, 416, 420; 424/9.1, 9.3; 436/173; 703/2
See application file for complete search history.

(56) References Cited

U.S. PATENT DOCUMENTS

| | | | |
|---|---|---|---|
| 5,694,934 A | 12/1997 | Edelman | |
| 5,706,805 A * | 1/1998 | Swartz et al. | 600/431 |
| 6,370,415 B1 * | 4/2002 | Weiler et al. | 600/410 |
| 6,589,506 B2 | 7/2003 | Cremillieux et al. | |
| 6,915,151 B2 * | 7/2005 | Baumgardner et al. | 600/420 |
| 7,072,706 B2 | 7/2006 | Baumgardner et al. | |

(Continued)

FOREIGN PATENT DOCUMENTS
EP    1588180 A1    10/2005

OTHER PUBLICATIONS

Y Ohno, H Hatabu, D Takenaka, M Van Cauteren, M Fujii, K Sugimara. Dynamic Oxygen-Enhanced MRI Reflects Diffusing Capacity of the Lung. Magnetic Resonance in Medicine 47: 1139-1144 (2002).*

(Continued)

*Primary Examiner* — Brian Casler
*Assistant Examiner* — Amanda Lauritzen
(74) *Attorney, Agent, or Firm* — Michael Best & Friedrich LLP

(57) ABSTRACT

The present invention relates to a method of characterizing lung function in a subject in need of such characterization. The method comprises performing an imaging technique, on a voxel defined within a lung space of interest. Image data is generated over a time period during which the subject inhales gases with at least two different partial pressures of a paramagnetic gas. A compartmental model algorithm is applied to the image data generated for the voxel to provide information on ventilation, diffusion and perfusion of a lung. The paramagnetic gas is preferably Oxygen. The imaging technique is preferably Oxygen Enhanced Magnetic Resonance Imaging (OE-MRI).

15 Claims, 15 Drawing Sheets

U.S. PATENT DOCUMENTS

| | | | |
|---|---|---|---|
| 7,867,477 B2* | 1/2011 | Driehuys et al. | 424/9.3 |
| 2002/0043267 A1* | 4/2002 | Weiler et al. | 128/898 |
| 2004/0129272 A1* | 7/2004 | Ganesh et al. | 128/207.14 |
| 2005/0022814 A1* | 2/2005 | Manhard | 128/204.18 |
| 2009/0120435 A1* | 5/2009 | Slessarev et al. | 128/203.14 |
| 2009/0246138 A1* | 10/2009 | Santosh et al. | 424/9.2 |
| 2010/0282258 A1* | 11/2010 | Tailor et al. | 128/204.23 |
| 2011/0104067 A1* | 5/2011 | Driehuys et al. | 424/9.3 |

OTHER PUBLICATIONS

XP002488377, Database Medline [Online], US National Library of Medicine (NLM), Bethesda, MD, US: Jun. 2002, Ohio Yoshiharu et al: "Dynamic oxygen-enhanced MRI reflects diffusing capacity of the lung." Database accession No. NLM12111960, p. 1140, left-hand column and p. 1143, left-hand column & Magnetic Resonance in Medicine: Official Journal of the Society of Magnetic Resonance in Medicine / Society of Magnetic Resonance in Medicine Jun. 2002, vol. 47, No. 6, Jun. 2002, pp. 1139-1144, ISSN: 0740-3194.

XP002488378, Database Medline [Online], US National Library of Medicine (NLM), Bethesda, MD, US; Aug. 2005, Naish Josephine H et al: "Improved quantitative dynamic regional oxygen-enhanced pulmonary imaging using image registration." Database accession No. NLM 16032679 cited in the application p. 465, paragraph 3 & Magnetic Resonance in Medicine: Official Journal of the Society of Magnetic Resonance in Medicine / Society of Magnetic Resonance in Medicine Aug. 2005, vol. 54, No. 2, Aug. 2005, pp. 464-469, ISSN: 0740-3194.

XP002488379, Database Medline [Online], US National Library of Medicine (NLM), Bethesda, MD, US; May 2004, Jakob Peter M. et al: "Assessment of human pulmonary function using oxygen-enhanced T(1) imaging in patients with cystic fibrosis." Database accession No. NLM15122684 cited in the application abstract & Magnetic Resonance in Medicine: Official Journal of the Society of Magnetic Resonance in Medicine / Society of Magnetic Resonance in Medicine, May 2004, vol. 51, No. 5, May 2004, pp. 1009-1016, ISSN: 0740-3194.

XP002380246, Tofts P S et al: "Estimating Kinetic Parameters From Dynamic Contrast-Enhanced T1-Weighted MRI of a Diffusable Tracer: Standardized Quantities and Symbols" Journal of Magnetic Resonance Imaging, Society for Magnetic Resonance Imaging, Oak Brook, II, US, vol. 10, No. 3, Sep. 1, 1999, pp. 223-232, ISSN: 1053-1807.

XP009103075, Seymour S. Kety: "The Theory and Applications of the Exchange of Inert Gas at the Lungs and Tissues" Pharmacological Reviews, Williams and Wilkins Inc., Baltimore, MD, US, vol. 3, Jan. 1, 1951, pp. 1-41, ISSN: 0031-6997.

XP009103081, Johnson and Wilson, "A model for capillary exchange" American Journal of Physiology, American Physiological Society, Bethesda, MD, US, vol. 210, Jan. 1, 1966, pp. 1299-1303, ISSN: 0002-9513.

Rijpkema, M. et al: "Effects of carbogen breathing on tissue oxygenation and perfusion in head and neck tumors as measure by MRI" Proceedings of the International Society for Magnetic Resonance in Medicine, 2001, p. 633, XP0025344470, section 'Patients and Methods', 1 page.

Jarrett F. et al: "The use of hypercapnia in the study of regional cerebral blood flow abnormalities with <133>Xe" Journal of Surgical Research, Academic Press Inc., San Diego, CA, US, vol. 32, No. 2, Feb. 1, 1982, pp. 104-109, XP023022583 ISSN: 0022-4804 [retrieved on Feb. 1, 1982] *p. 104, section 'Introduction', last sentence* p. 104, col. 2, line 13—p. 105, col. 1, line 2, 6 pages.

Fiat D. et al: "In vivo 17O NMR study of rat brain during 17O2 inhalation." Magnetic Resonance in Medicine: Official Journal of the Society of Magnetic Resonance in Medicine/Society of Magnetic Resonance in Medicine Apr. 1992, vol. 24, No. 2, Apr. 1992, pp. 370-374, XP002534471 ISSN: 0740-3194 *section 'Introduction', second paragraph * p. 371, lines 4-7 * p. 372, equation [1]*, 6 pages.

PCT/GB20091000979 International Search Report and Written Opinion dated Jul. 9, 2009, 15 pages.

* cited by examiner

(a) Non-smoker:

Parameter Maps

Histograms

(b) Smoker:

Parameter Maps

Histograms

(a)

(b)

OXYGEN-ENHANCED MAGNETIC RESONANCE IMAGING TECHNIQUE AND COMPARTMENTAL MODEL ALGORITHM

The present invention relates to methods for imaging the lungs and in particular to the application of a compartmental model to (but not limited to) Oxygen-Enhanced Magnetic Resonance Imaging (OE-MRI).

Nuclear magnetic resonance (NMR) involves applying a magnetic field that acts on the nuclei of atoms with fractional spin quantum numbers and thereby polarizes them. During measurements, radio-frequency pulses of given resonance energy are applied that flip the nuclear spins and disturb the orientation distribution. The nuclei then return (relax) to the initial state in a time dependent exponential fashion and thereby give a signal that may be electronically processed into recordable data. When the signals are spatially differentiated and of sufficient level, the data can be organized and displayed as images on a screen. For instance, computing the signals generated by the protons of water within organic tissues makes it possible to construct magnetic resonance images (MRI) allowing direct visualization of internal organs in living beings. NMR is therefore a powerful tool in diagnostics, medical treatment and surgery.

It will be appreciated that a clinician will wish to test lung function for a number of reasons. By way of example, it can be informative to characterise lung ventilation because such ventilation can be affected by a range of obstructive pulmonary disorders. Currently, standard lung function tests can assess a wide range of global variables describing lung physiology but cannot be used to investigate disease regionally. Scintigraphy is used for functional imaging but the technique necessitates the inhalation of radioactive substances; is limited by low spatial resolution; and is not tomographic.

Until relatively recently, MRI has been limited in its application to the lung because of the intrinsically low proton density, the large susceptibility differences and respiratory and cardiac motion. Hyperpolarized gas MRI using $^3$He or $^{129}$Xe has shown the possibility for detailed regional assessment of lung function but the high costs and specialized equipment involved have limited its use in a clinical setting. OE-MRI has been demonstrated in both healthy volunteers and patients with pulmonary disease as an alternative, indirect method to visualize lung ventilation. Molecular oxygen is paramagnetic and so acts as an NMR contrast agent when dissolved in parenchymal water due to its effect on $T_1$ ($T_1$ is known to those skilled in the art of NMR as the named spin-lattice relaxation time and is the time constant in the z-direction, which is taken to be parallel with the applied magnetic field). Breathing 100% oxygen results in an increase in the concentration of dissolved oxygen in the lung tissue producing a corresponding decrease in $T_1$ which can be detected as a regional signal intensity increase in a $T_1$-weighted image. Pixel-by-pixel analysis is made difficult by the change in size and shape of the lungs from one image to the next due to breathing. Breath-holding has been used in some studies but in patients with lung disease this can be uncomfortable and, as a result, difficult to perform in a reproducible manner. It may also be argued that breath-holding interferes with the phenomena being assessed since it requires large static inhalations which may lead to spurious interpretation of normal breathing diffusing capacity. According image registration methods have been developed to correct for breathing motion (e.g. see Naish et al. (2005) Magnetic Resonance in Medicine 54:464-469). Such methods allow registration of a lung outline and subsequent application of the registration to lung images leads to a significant improvement in the determination of regional oxygen-induced changes in $T_1$ and the time course of regional signal intensity change during oxygen wash-in and wash-out.

Naish et al (supra) and others (Ohno Y et al, (2002) Magnetic Resonance Medicine, 47, 1139, Jakob P M et al, (2004) Magnetic Resonance Medicine, 51, 1009-1016) have demonstrated that OE-MRI may be used to assess lung function by measuring the enhancement ratio between breathing air and 100% oxygen, and also by measuring the time to saturation of the increased signal effect (i.e. the oxygen wash-in rate, and also the oxygen wash-out rate). However, these constants give non-specific information on lung ventilation, diffusion and perfusion, leading to difficulties in interpretation of any differences in uptake characteristics in terms of physiologically-relevant processes. It therefore remains a problem that conventional OE-MRI is only able to provide limited information that may help a clinician give a reasoned diagnosis or prognosis.

Published US patent application U.S. Pat. No. 5,694,934A describes a method of acquiring images of the lungs for direct interpretation by a radiologist. The method uses the weakly paramagnetic effect of dissolved oxygen on the $T_1$ relaxation time of lung tissue, as detected by an MR imager. When oxygen is ventilated into the lungs, the paramagnetic effect of the Oxygen enhances the signal in a $T_1$ weighted MR scan of areas of the lungs into which the Oxygen has dissolved. According to the method described in U.S. Pat. No. 5,694,934A therefore, a first $T_1$ weighted image is generated before the oxygen has been absorbed into the lungs and a second $T_1$ weighted image is generated after the oxygen has been absorbed into the lungs. The two images are then interpreted and compared by a medical professional. Areas in the second, oxygen enhanced, image in which the signal does not appear to have been enhanced are interpreted by the medical professional as not having been ventilated, which indicates a problem in that area of the lung.

The two images produced by the method described in U.S. Pat. No. 5,694,934A relate only to the presence or absence of dissolved oxygen at locations within the lungs. This information alone is of limited diagnostic value because it is only an indication of whether, and to what extent, oxygen has dissolved into each area of the lungs. As described in U.S. Pat. No. 5,694,934A, the information is merely a novel indicator of lung ventilation and may be used in place of other tests which would indicate lung ventilation.

Published European Patent Application EP1588180A1 describes a method of obtaining dynamic data sets from NMR spectroscopy scans of the lungs of a subject by introducing hyperpolarised $^{129}$Xe as a contrast agent by causing the subject to inhale the polarised $^{129}$Xe. The method involves directly detecting hyperpolarised $^{129}$Xe in each of a gaseous, a water-dissolved and a blood-dissolved state within the lungs. The three types of detected data are analysed so as to create dynamic data sets, which may contain information about, for example, tissue thickness, blood compartment thickness, perfusion or alveolar radius. Unfortunately the method involves the inhalation of a noble gas and a breath hold, which has well documented potential risks to the patient, particularly patients with suspected lung pathology. Breath hold techniques are also known to be a cause of errors in the measurement of lung function, because the lungs are not functioning as they normally would at the time of measurement. Also, a subject does not usually breathe hyperpolarised $^{129}$Xe so results from this kind of scan do not show dynamic datasets of the lungs under normal working conditions, i.e. breathing a gas mix which contains oxygen.

Use of a hyperpolarised gas incurs costs in creation, transport, storage and administration of the gas to the patient. $^{129}$Xe that is not hyperpolarised produces little or no signal in an NMR spectroscopy scan. The process for polarising $^{129}$Xe commonly includes mixing the $^{129}$Xe with an alkali vapour, which would be damaging to a live subject. The alkali vapour must therefore be removed before the hyperpolarised $^{129}$Xe may be administered to the subject at a cost to ease and efficiency. Also, because hyperpolarised $^{129}$Xe depolarises over time, the substance has a limited shelf-life after which time it becomes useless for the purpose described in EP 1588180 A1. Storage of the $^{129}$Xe so as to prolong the polarisation period is also costly and inefficient, as is the re-polarisation of $^{129}$Xe which has depolarised. These factors add to the great inconvenience associated with this kind of scanning.

It is therefore an object of the present invention to overcome problems associated with prior art scanning methods (e.g. OE-MRI methods) and provide a technique that will provide clinically significant information about lung function and physiology in the health and diseased states.

According to a first aspect of the present invention there is provided a method of characterising lung function in a subject in need of such characterisation comprising:
  performing an imaging technique, on a voxel defined within a lung space of interest,
  wherein image data is generated over a time period during which the subject inhales gases with at least two different partial pressures of a paramagnetic gas,
  and applying a compartmental model algorithm to the image data generated for the voxel to provide information on ventilation, diffusion and perfusion of a lung.

The imaging technique may be any appropriate imaging technique known to the skilled person. For instance it may be any form of MRI, CT scanning, X-ray etc. However it is preferred that the imaging technique is MM.

The paramagnetic gas may be any appropriate paramagnetic gas although it is preferred that the paramagnetic gas is Oxygen.

When the imaging technique is MRI it is preferred that the paramagnetic gas is Oxygen. Alternatively, when MRI is used, the paramagnetic gas may be an aerosol or other contrast media such as gadolinium-based aerosols that cause a signal change in the lung parenchyma when observed with MRI.

It is most preferred that the imaging technique is Oxygen-Enhanced Magnetic Resonance Imaging (OE-MRI).

It is preferred that the image data provides information in respect of ventilation, diffusion across the alveolar membrane and/or perfusion of a lung.

The method of the first aspect of the invention allows lung function to be evaluated and provides important data that is useful for making a diagnosis and also giving a prognosis for subjects with lung damage or disease (e.g. subjects with pulmonary fibrosis, subjects with obstructive lung conditions, smokers, asthmatics and the like) or those who are predisposed to such damage or disease (e.g. from environmental causes or for genetic reasons).

By the term "voxel" we mean a volume element in a grid defined by 3-dimensional space within the lung volume. The size of a voxel is scalable and may comprise the whole lung. However, in the present invention, it is preferred that each lung is divided into a matrix of voxels that are each typically a few cubic millimetres.

The present invention is based upon the inventors' knowledge in the field of MRI, and particularly OE-MRI, and image processing. They have appreciated that OE-MRI is useful for visualising the lung because molecular oxygen is effectively non MRI-visible in gaseous form when using $^1$H MR imaging (e.g. in the bronchi or the alveolar space) but when in an aqueous environment (e.g. in the interstitial fluid, inside cells or in plasma) will interact with protons in water and therefore result in an altered NMR signal. The present invention was made when the inventors were considering whether or not these MRI properties of molecular oxygen would make it possible to obtain meaningful data relating to pulmonary function from OE-MRI. They realised that the difference in MRI-visibility between molecular oxygen in the gaseous and aqueous/lipid phase may allow them to use OE-MRI to measure the rates at which oxygen was removed from the alveoli gaseous space into to the fluid of the alveolar membrane, interstitial spaces and alveolar capillaries, and finally removed from the alveolar capillaries when taken into the body via the blood stream. Such data would be of great value because they would provide a clinician with informative data regarding the health status of a subject's lungs. A clinician will appreciate that there are numerous situations (e.g. obstructive pulmonary disease) where either the efficiency of ventilation along the airways to the alveoli, or diffusion of oxygen at the alveoli, or perfusion of the lung is compromised (or indeed any combination of these), and that a technique for visualising areas of the lung suffering impairment in any of these aspects of function would be very powerful for making a diagnosis or prognostic assessment.

The inventors further realised that OE-MRI could be a powerful technique because the voxel size could be set quite small and NMR used to visualise the whole of the lung by detecting an NMR signal from a matrix of voxels that fill the whole space of the lung or a proportion thereof. Accordingly the method of the invention preferably involves conducting OE-MRI on "n" voxels forming a matrix within the lung space. The efficiency of gaseous exchange can be measured for each voxel and a clinician may then be presented with specific information on ventilation, diffusion and perfusion in discrete areas of a lung.

The inventors appreciated that the best way of calculating the rate of oxygen transfer would be to analyse the transfer of oxygen from the alveolar gaseous space (a first compartment) into the tissues (a second compartment) by continuous dynamic acquisition of NMR data from alveoli while the gas supply was switched between gas mixtures of varying partial pressures of oxygen, resulting in a gradual variation in the concentration of gaseous oxygen arriving at the alveoli. In principle, this may be achieved by requiring a subject to breathe in at least two different concentrations of oxygen. The MRI data collected when the lungs are ventilated with the different concentrations of oxygen can be used to calculate the rate of oxygen ventilation through the airways and transfer across the alveolar membranes using the algorithm discussed in more detail below.

A further important factor that contributed to the realisation of the invention is that the inventors appreciated that much of the oxygen that is transferred across the alveolar walls is rapidly transported way from the lungs via the venous network and ultimately in the pulmonary vein. Accordingly this effect is factored into the algorithm used according to the invention.

Subjects tested according to the method of the invention may be any subject for which it is desirable to test lung function. The subject is preferably a mammal (although the methodology is also generally applicable to any organism with a lung, such as birds, reptiles, amphibians) and the method is particularly suitable for testing lung function in animals of veterinary importance (e.g. horses, cattle, dogs or cats), or animals important in therapeutic (including but not limited to pharmacological) development work (e.g. mice or rats). However it will be appreciated that the subject is preferably a human.

The method is particularly useful for testing human subjects with conditions such as asthma, chronic obstructive lung disease, fibrotic lung diseases, emphysema, bronchitis, alpha1-antitrypsine deficiency and bronchiectasis or in the case of airway constriction or alveolar damage caused by smoking or environmental factors.

Subjects to be tested should be placed in an MRI machine typically but not necessarily at 1.5 Tesla magnetic field strength. As the method requires little specialist equipment it should be possible to use OE-MRI in any MRI machine designed for human or animal use. A $T_1$-weighted imaging protocol should be chosen which is suitable for lung imaging, i.e. which can overcome the problems caused by low proton density in the lung and the magnetic field in homogeneity induced by the many air-tissue interfaces of the lung, and one which is also sufficiently sensitive to the signal changes induced by changes in inhaled oxygen concentration, e.g. an Inversion Recovery Half Fourier Single-Shot Turbo Spin-Echo (IR-HASTE) sequence, or an Inversion Recovery Snapshot Fast Low Angle-Shot (IR Snapshot FLASH) sequence. Gases are typically delivered at a rate of 10-15 l/min. Most preferred NMR parameters are provided in the methods section of Example 1.

The subject inhaling gases with at least two different partial pressures of a paramagnetic gas may be fitted with a mask or breathing apparatus for gas delivery in order that different gases may be inhaled while the MRI scans are performed. When the gas is oxygen room air may be used as one of the partial pressures of oxygen in which instance the subject would breathe normally without the use of any apparatus.

It is preferred that the subject inhales two gases—a first gas has a relatively low concentration of oxygen (e.g. 10%-35%) and the other gas contains a relatively high concentration of oxygen (e.g. 45%-100%). It is most preferred that the first gas is air (comprising approximately 21% oxygen) and the other is a gas comprising an oxygen content of 90%-100%. It will be appreciated that the choice of gases used may depend on the health status of the subject.

Before the beginning of a scan using dissolved oxygen as a contrast agent, the concentration of dissolved oxygen within the lungs of a live subject is always greater than zero because the subject has been continuously breathing air. This is different to imaging techniques in which artificial contrast agents such as hyperpolarized $^{129}$Xe are used because hyperpolarized $^{129}$Xe is not a naturally occurring substance, so the concentration of $^{129}$Xe in the lungs of a subject before a scan can be assumed to be zero. Providing a first gas, of a first concentration of oxygen, allows signals to be detected for dissolved oxygen concentration within the lungs. Providing another gas, of a different concentration, during scanning allows the changes in dissolved oxygen concentration to be detected during a transition period in which the alveolar spaces fill with the other gas and the increased concentration of oxygen within the other gas is dissolved into the lungs. Further measurements may then be made during breathing of this gas.

The subject may revert back to breathing the first gas. In this event, measurements are preferably made which detect the change in concentration of dissolved oxygen within the lungs during this further transition period. Transitions between each gas may be repeated as needed. This method provides a more accurate measurement of local concentrations of oxygen within the lung than can be obtained simply by measuring dissolved oxygen concentration for a single gas.

The time taken for a transition from a lower to a higher concentration of oxygen in the alveolar spaces is known as the "wash in" time. The time taken for a transition from a higher to a lower concentration of oxygen in the alveolar spaces is known as the "wash out" time. The length of wash in time and wash out time are approximately equal for a single subject during a single scanning period and, accordingly, the approximate length in seconds of the wash in and wash out times for a single subject during a single scanning period is indicated herein by a single value ($T_{VENT}$).

It is preferred that OE-MRI data is recorded for each voxel by starting a subject on a low concentration of oxygen; swapping the inhaled gas to one with a high oxygen concentration for a period of time; and then returning the subject to inhaling the low oxygen concentration gas again. The method of the invention most preferably generates OE-MRI data from a subject wherein 100% oxygen is washed-in and washed-out when individuals are breathing normal air (e.g. medical air comprising 21% oxygen) before and after the 100% oxygen is inhaled. The differing concentrations of the oxygen, acting as a contrast medium, then influence the NMR signal detected from protons (primarily from water or lipids in the pulmonary tissue) if proton NMR is being employed but potentially other NMR-visible nuclei if non-proton MRI is being employed, and this OE-MRI data is then used to create the input for the algorithm used according to the invention. Most preferred regimens are described in the examples.

In individuals with healthy lung function the Oxygen-Enhanced MRI signal of the lung will have increased and reached saturation within approximately 5 min. The time for the signal to decrease to its normal baseline value when the gases are switched back to air is also within the same time frame of approximately 5 min. Typically the subject will be required to breathe a gas mixture or mixtures with a higher concentration of oxygen for a maximum period of approximately 10 minutes. Adverse effects from breathing higher concentrations of oxygen have only been noted after approximately 24 hours exposure, and therefore this length of exposure is deemed safe and without any detrimental effects for the majority of subjects.

A major challenge using NMR in the lungs is the problem caused by the movement and expansion of the lungs during breathing and also by the movement caused by the beating of the heart. This causes a technical challenge when an MRI signal needs to be measured from a single voxel over time. It is therefore preferred that image registration techniques are applied to ensure that measurements can be made from the same volume of tissue. It is preferred that the image registration techniques developed by Naish et al. are used according to the method of the invention (Naish et al. (2005) Magnetic Resonance in Medicine 54:464-469).

The invention has been based on the realisation that a compartmental modelling approach may be applied to OE-MRI to allow the extraction of parameters from the enhancement information that give more specific information on local ventilation, diffusion and perfusion. The compartmental model may be based on a first compartment which is the alveolus space (containing non-MRI visible gaseous oxygen) and a second compartment (including the alveolus membrane, interstitial space between the membrane and pulmonary capillaries and the plasma within the capillaries), containing oxygen dissolved in water with a combined oxygen concentration, that will determine the NMR signal from the voxel which contains the alveolus (see FIG. 1).

The model applied to the data is preferentially a compartmental model although it will be appreciated that similar methods, such as distributed parameter models, may also be used. Accordingly similar methods, such as distributed parameter models, fall within the definition of "a compartmental model algorithm" as used herein. For instance the methods according to the invention may utilise a distributed parameter model, according to principles described in Johnson J A, Wilson T A. A model for capillary exchange. Am J Physiol 1966; 210(6):1299-1303 instead of the compartmental models discussed below.

It will be appreciated that the development of such a model represented considerable technical hurdles. The inventors therefore applied considerable inventive endeavour to develop a compartmental model for OE-MRI of the lung that allows the calculation of parameters describing efficiency of lung ventilation, the rate of diffusion across the alveolar membranes and the rate of blood flow through pulmonary capillaries.

One particular realisation of the inventors has been that the compartment model may be used to calculate such parameters in the absence of detected signal values in at least one of the compartments, namely the value of the concentration of oxygen within the alveolar space ($C_A$). This is in direct contrast to prior uses of compartmental models for interpreting scan data, in which the values of individual compartments are read and the function of the compartmental model is merely to infer transmission parameters between the compartments based on the changes in value of each compartment. In general an advantage of this method is the ability to infer the contents of a compartment of the model from the contents of the other compartments. Specifically, in the case of OE-MRI, an advantage is that gaseous oxygen which is not visible in the alveolar space, may be inferred from the oxygen that is delivered in a controlled manner to the subject by a breathing mask and the lag time for the oxygen to be transferred to the alveolar space may be inferred from the values of oxygen which has dissolved into the tissues and blood surrounding the alveolar space.

The method according to the invention is preferably a two-compartment model based on known physiological parameters for rate of oxygen diffusion across alveoli membranes and pulmonary blood flow. Such a compartmental model preferably models the combined oxygen concentration of a second compartment comprising the alveolus membrane, interstitial space between the membrane and pulmonary capillaries and the plasma within the capillaries ($C_p$) obtained from the changing NMR signal values. This may be achieved by calculating the change in $T_1$ spin-lattice relaxation time, which causes the signal change, and by converting the change in $T_1$ time through known constants of proportionality to the change in dissolved oxygen concentration.

It is also preferred that the compartmental model takes into account one or more of the following parameters, or facilitates the calculation of such parameters: the fractional volume of blood plasma and tissue water per MRI visible tissue ($V_p$); diffusing capacity of the alveolar membrane ($K_{ox}$); the extraction fraction of oxygen from the tissue water and capillaries (E); the rate of blood flow in the capillaries ($F_b$) and also the parameters describing the shape of the input function which defines the predicted oxygen concentration arriving at the alveolus (i.e. the time-lag between inhalation of an elevated level of oxygen and the maximum input oxygen concentration within the alveolus, or ventilation time).

It is particularly preferred that the compartmental model takes into account the amount of Oxygen in the alveolar space, the amount of dissolved Oxygen in the area of the lungs (indicated by the detected signal by the imaging scan), the rate at which oxygen is dissolved into the tissues and blood within the lungs, and also the rate at which the dissolved oxygen is removed from the area of the lungs by the blood. The model preferably indirectly accounts for the amount of Oxygen in the alveolar space as this value cannot be determined directly. The realisation that this part of the compartmental model does not need to be detected by an imaging scan was a major technical hurdle which was overcome during the development of a compartmental model for use with oxygen enhanced MRI.

The model allows the calculation of these parameters using any algorithm (such as the Levenberg Marquardt non-linear least squares fitting algorithm) that allows the fitting of the functional form described by the compartmental model $C_p$ (see equation II) to the dynamic oxygen concentration dataset calculated from the changing NMR signals in the pulmonary water.

The model used according to the invention may be based on a number of compartmental models, such as a three compartment model which again assigns the gaseous space of the alveolus as the first compartment, but this time the alveolus membrane and interstitial fluid comprises the second and the plasma within the alveolar capillaries is assigned as a third separate compartment.

It is preferred that the compartmental model is an adaptation of the equations developed by Kety (Kety, SS (1951) Pharmacological Reviews. 3: 1-41) who described the rate of diffusion of gases across the alveolus membrane to pulmonary capillary blood.

Therefore the method of the first aspect of the invention preferably applies a compartmental model algorithm based on the Kety two compartment model. The algorithm is applied to OE-MRI data obtained by washing-in and washing-out inhaled gases with at least two different partial pressures of oxygen. Preferably MRI measurements will be made on a subject who starts breathing normal air (21% oxygen); 100% oxygen is then washed-in and maintained for defined time period (e.g. 5 minutes); and the 100% oxygen is then washed-out by returning to breathing normal air (21% oxygen). The differing concentrations of the oxygen, acting as a contrast medium, then influence the NMR signal detected from protons (primarily from water in the pulmonary tissue) and this OE-MRI data is then used as a function to be fitted by a two-compartment model according to the invention.

It will be appreciated that a number of different algorithms may be developed for use according to the method of the first aspect of the invention. It will be further appreciated that one reason for an inventive step of the method of the invention is that the inventors were the first to appreciate that a compartmental model could be applied to OE-MRI data from the lung (despite the problems associated with such techniques).

In a preferred embodiment of the invention, the inventors developed an algorithm by applying the following proof:

The first compartment is the alveolus space and the oxygen concentration may be denoted by $C_A$, and the second compartment includes the alveolus membrane, interstitial space between the membrane and pulmonary capillaries and the plasma within the capillaries, with a combined oxygen concentration denoted by $C_p$ (see FIG. 1).

The inventors then developed a model by assuming near saturation of oxygen in arterial haemoglobin during air breathing, which would result in extra oxygen being carried mainly in the plasma when 100% oxygen breathing occurs. In lung the increased signal occurs in the parenchymal water and capillary blood, and therefore the measured increased concentration can be considered equivalent to $C_p (\propto [(T_1^{O_2})^{-1} -$ $(T_1^{Air})^{-1} = R_1^{O_2} - R_1^{Air}]$). Using these approximations the inventors developed equation (I):

$$V_p \frac{dC_p}{dt} = K_{ox}(C_A - C_p) - EF_b C_p, \qquad (I)$$

where $V_p$ is the fractional volume of blood plasma and tissue water per MRI visible tissue, $K_{ox}$ is a term describing the diffusing capacity of the alveolar membrane, E is the extraction fraction of oxygen from the tissue water and capillaries, and $F_b$ is the rate of blood flow in the capillaries. Based on these calculations the inventors realised that it would be possible to solve $C_p$ (i.e. the combined oxygen concentration of the second compartment comprising the alveolus membrane, interstitial space between the membrane and pulmonary capillaries and the plasma within the capillaries, calculated as described above) using equation II:

$$C_p = \frac{K_{ox}}{V_p} \int C_A(\tau) \exp\left(-\frac{K_{ox} + EF_b}{V_p}(t - \tau)\right) d\tau. \qquad (II)$$

Clinically meaningful information may be attached to values for $EF_b$ and $K_{ox}$ and the lag time to maximum oxygen concentration in the gaseous alveolar space and data is present from pulmonary regions and also as parameter maps from a coronal section of the lung in the examples.

The method of the present invention is particularly useful for both prognostic and diagnostic purposes in respiratory conditions. However, in a preferred embodiment the method will be of particular use in prognostics and in the development and monitoring of drug therapies. Prognostic use could also include the identification of patients who are more or less likely to respond to a given treatment option, which could enhance patient selection criteria for therapy.

This technique of measuring regional lung function will allow the measurement of ventilation impairment, damage of the alveoli membrane or structure and also assessment of pulmonary perfusion and a broad variety of diseases and conditions including but not limited to emphysema, bronchitis, asthma, chronic obstruction pulmonary disease, bronchiectasis, byssinosis, bronchiolitis, asbestosis, fibrosis, hypersensitivity pneumonitis, smoking induced lung damage and pneumonia as well as pulmonary vascular conditions such as pulmonary embolisms.

It will be appreciated that the method of the invention has many advantages over prior art techniques. Prior to this invention, other workers, such as the inventors of U.S. Pat. No. 5,694,934 A, analysed the OE-MRI signal by simplistic comparisons of the magnitude of signal change achieved at varying oxygen concentrations and/or the time taken for the signal to achieve maximum enhancement or the time for the signal to fall back to baseline. These simplistic approaches did not take into account the complex underlying interaction of lung ventilation, alveolar diffusion and pulmonary perfusion which combined to create the enhanced signals measured.

A major advantage of the invention is that a clinician does not need to conduct any time consuming conventional tests to obtain data relating to lung function, such as spirometry measurements or diffusing capacity (DLCO) tests, which are noted to be sometimes not very reliable or reproducible and cannot in any case provide regional information. The method enables a person conducting the test to perform quick, relatively standard MRI (albeit the subject needs to wear a mask for supply of the first and further gases containing different concentrations of oxygen) and can very rapidly-generate an image of the lung function.

It should be noted that the concept of a compartmental model applied to imaging of lung function is also applicable to other gases or aerosols that may be breathed by the patient and that cause a subsequent change in the signal observed in the lung parenchyma.

It will be appreciated that the use of a compartmental model, in conjunction with measurements of the concentration of dissolved parenchymal oxygen and an input function, allows the derivation of physiological parameters that have values that are independent of the scanning machine or data acquisition method (although it is acknowledged that these factors may affect the quality of the derived parameters).

This is an advantage over methods that seek to measure oxygen enhancement ratios or wash-in rates based on NMR signal or $T_1$ values, each of which can be dependent upon the choice of field strength, the nature of the gas or aerosol, and NMR data acquisition technique.

A further advantage of using oxygen as a contrast agent is that it is non-toxic and requires no specialist preparation beyond the provision of a supply of pure oxygen. Other possible contrast media that could be used in a compartmental model are generally of a specialist nature (for example gadolinium-based aerosols), making them a less practical option than oxygen. Additionally, oxygen may be breathed comfortably for many minutes without any practical or physiological complications. Other possible media (for example gadolinium-based aerosols) are generally limited to a single breath administration, which would limit their practical utility.

It will be appreciated that the methods according to the first aspect of the invention (described above) may be adapted to evaluate lung function using any imaging technique that allows the assessment of the quantities of any gas, aerosol or other contrast medium that can be delivered to the lungs in breathable form and becomes measurable only once it has dissolved in the pulmonary fluid, and that is subsequently washed away by the pulmonary blood supply. This may include any other paramagnetic gases, aerosols and other contrast media such as gadolinium-based aerosols that cause a signal change in the lung parenchyma when observed with MRI. This may also involve other imaging modalities with appropriate contrast media that are only detectable once dissolved in the pulmonary water.

According to a second aspect of the invention there is provided a computer apparatus for generating data concerning lung function, the apparatus comprising:
 a memory storing processor readable instructions; and
 a processor configured to read and execute instructions stored in said memory;
 wherein said processor readable instructions comprise instructions controlling said processor to apply the algorithm defined in the first aspect of the invention to lung image data.

The apparatus according to the second aspect of the invention may comprise computational hardware and a display device required to calculate and display the outputs following the application of the algorithm. The hardware and display device may either be separate entities to the scanning device used in the method (e.g. an MRI scanner) or may be integrated within the scanner, as is the case for many biomedical digital imaging systems such as an MRI scanner. Therefore the computer apparatus may be part of a scanning apparatus.

It will be appreciated that computer software may apply the algorithm required to fit the model to the raw OE-MRI data and convert the output parameters to histograms or maps of lung function, or to regional average values. Such histograms and maps are routinely generated for MRI (e.g. see FIG. 4 or 5). The manipulation of OE-MRI data with such software has the advantage that data from large numbers of voxels can be quickly manipulated, without user input, to provide a detailed image of function across the whole lung or a region thereof.

The algorithm of the invention may be embodied within computer software and may be implemented using a computational hardware and display device that is separate to the imaging device or integral to it. Such software represents a further aspect of the invention and according to a third aspect of the invention there is provided a carrier medium carrying computer readable program code configured to cause a computer to carry out a method of applying an algorithm as defined in the first aspect of the invention.

It will be appreciated that a computer program embodying the invention may be provided in any desirable manner. Such a computer program in any form represents a further aspect of the invention and according to a fourth aspect of the invention there is provided a computer program configured to cause a computer to carry out a method of applying an algorithm as defined by the first aspect of the invention.

Software according to the fourth aspect of the present invention may be provided in any desirable programming language including Java™ (Sun Microsystems, Inc. 901 San Antonio Road Palo Alto, Calif. 94303, USA), C++(One Microsoft Way Redmond, WA 98052-6399, USA) or Matlab (The MathWorks, Inc. P.O. Box 845428 Boston, Mass., USA).

A user of software in accordance with the present invention would preferably obtain the software and install the software on an appropriate computer system which is configured to receive suitable MR image data, such as OE-MRI data.

Embodiments of the invention will now be further described, by way of example only, with reference to the following example and figures in which:—

FIG. 1: illustrates a two-compartment model for transfer of oxygen in the lung using OE-MRI: The first compartment is the alveolus with an effective oxygen concentration $C_A$ which is proportional to the gaseous partial pressure concentration $P_AO_2$ and within which the oxygen has negligible effect on the NMR signal. A constant $K_{ox}$ describes the rate of diffusion to and from the second compartment comprising of the membrane, interstitial space and the blood plasma within the alveolar capillaries, within which the oxygen alters the NMR signal. Oxygen is extracted from the second compartment at a rate defined by the extraction fraction E times rate of blood flow $F_b$ FIG. 2a: represents predicted wash in and wash out times ($T_{VENT}$) for a given change in partial pressure of Oxygen breathed by a subject ($PO_2$).

FIG. 2b: illustrates a compartmental model fit to the estimated average tissue $PO_2$ (difference above baseline air-breathing) of a region of interest at the top of the right lung of a subject as discussed in Example 1. The alveolar oxygen input function is also illustrated.

FIG. 3: represents maps of the compartmental model parameters obtained in the right lung of one individual as discussed in Example 1. Map (a) illustrates with a rainbow colourmap the extraction fraction multiplied by blood flow and demonstrates a regional variation over the lung, with lower values towards the top of the lung and at the periphery. Map (b) illustrates the results of Map (a) using a greyscale colourmap. If E is assumed equal to 1, the $F_b$ values are consistent with those reported in the literature. Map (c) shows the distribution of $K_{ox}$, which is mainly uniform apart from apparent clusters of higher ventilation in the centre of the lung using the rainbow colourmap. Map (d) shows the results of Map (c) using a greyscale colourmap. Map (e) shows the variation in time to achieve maximum $PO_2$ in the alveoli, with central areas achieving times close to the predicted value of 1 minute, while at the lung periphery values of up to 2 minutes were obtained. Map (f) shows the results of Map (e) using a greyscale colourmap.

FIG. 4: represents maps and histograms of the compartmental model parameters obtained in the right lung of (a) a non-smoker; and (b) a smoker as discussed in Example 2.

FIG. 5: represents histograms of averaged data of the compartmental model parameters obtained in the right lung of (a) a group of non-smokers; and (b) a group of smokers as discussed in Example 2.

FIG. 6: represents modeled values for the concentration of Oxygen in the second compartment ($C_r$) in a particular exemplary embodiment. Detected signal values for concentrations of Oxygen $C_e$ are also shown.

FIG. 7: represents a box plot of results from an analysis of $K_{ox}$ of a number of test subjects in the third example.

FIG. 8: represents a box plot of results from an analysis of $EF_b$ of a number of test subjects in the third example.

FIG. 9: represents a box plot of results from an analysis of the wash in time $T_{VENT}$ to reach a maximum concentration of Oxygen in the lung tissues and blood of a number of test subjects in the third example.

FIG. 10: represents image maps of values for a) $K_{ox}$, b) $EF_b$ and c) $T_{VENT}$ for the lung of a healthy non-smoking subject.

FIG. 11: represents image maps of values for a) $K_{ox}$, b) $EF_b$ and c) $T_{VENT}$ for the lung of a smoking subject with a healthy spirometry.

FIG. 12: represents image maps of values for a) $K_{ox}$, b) $EF_b$ and c) $T_{VENT}$ for the lung of an unhealthy smoking subject.

FIG. 13: represents a correlation plot between values of $K_{ox}$ modelled by a method according to the present invention and PS generated from standard Dynamic Contrast Enhanced MRI (DCE-MRI). Each data point is signified as belonging to a smoker (square points) or a non-smoker (circular points).

FIG. 14: represents a correlation plot between values of $EF_b$ modelled by a method according to the present invention and PS generated from standard DCE-MRI. Each data point is signified as belonging to a smoker (square points) or a non-smoker (circular points).

EXAMPLE 1

The method of the first aspect of the invention was developed and applied to measure lung function of a group of normal individuals.

1.1 Methods (a) Image Acquisition

The images used in this study were obtained from five normal consented volunteers, (two males, three females, ages 30-39), using a 1.5 T Philips Gyroscan NT Intera MR system (Philips Medical Systems, Best, Netherlands). Subjects breathed medical air or 100% oxygen through an MR compatible Bain breathing system (Intersurgical Ltd., Wokingham, UK) and tightly fitting mask. A standard anesthesia trolley (10 l/min capability) was used. A first set of images was acquired in order to measure $T_1$ during air-breathing A half Fourier single shot turbo spin-echo (HASTE) sequence was used with 68 phase encoding steps and inter-echo spacing of 4 ms, effective echo time 16 ms, 128×128 matrix with field of view 450×450 mm², coronal section with slice thickness 10 mm. $T_1$ measurements were performed using a saturation recovery HASTE sequence with saturation times ($T_{SAT}$) of 100, 200, 400, 800, 1200, 1700, 2300, 3000, 3500 ms. Five images were collected for each saturation time to enable averaging over the cardiac cycle. Saturation recovery (SR) was chosen here to give a shorter total imaging time. Next, dynamic image acquisitions were performed using an IR HASTE sequence with an inversion time of 720 ms (chosen to approximately null the signal from the lungs while breathing air). The gas supply was switched from medical air to 100% oxygen after the tenth image in the series. A set of $T_1$ measurement SR images was acquired while the subject continued to breathe 100% oxygen. Finally a second series of dynamic images was acquired with the gas supply being switched back to medical air after the tenth image.

(b) Compartment Model

The first compartment is the alveolus space and the oxygen concentration may be denoted by $C_A$, and the second compartment includes the alveolus membrane, interstitial space between the membrane and pulmonary capillaries and the plasma within the capillaries, with a combined oxygen concentration denoted by $C_p$ (see FIG. 1).

The inventors then developed a model by assuming near saturation of oxygen in arterial haemoglobin during air breathing would result in extra oxygen being carried mainly in the plasma when 100% oxygen breathing occurs. In lung the increased signal occurs in the parenchymal water and capillary blood, and therefore the measured increased concentration can be considered equivalent to $C_p (\propto [(T_1^{O_2})^{-1} - (T_1^{Air})^{-1} = R_1^{O_2} - R_1^{Air}])$. Using these approximations the inventors developed equation (I):

$$V_p \frac{dC_p}{dt} = K_{ox}(C_A - C_p) - EF_b C_p, \qquad (I)$$

where $V_p$ is the fractional volume of blood plasma and tissue water per MRI visible tissue, $K_{ox}$ is a term describing the diffusing capacity of the alveolar membrane, E is the extraction fraction of oxygen from the tissue water and capillaries, and $F_b$ is the rate of blood flow in the capillaries. Based on these calculations the inventors realised that it would be possible to solve $C_p$ (i.e. the combined oxygen concentration of the second compartment comprising the alveolus membrane, interstitial space between the membrane and pulmonary capillaries and the plasma within the capillaries calculated as described above) using equation II:

$$C_p = \frac{K_{ox}}{V_p} \int C_A(\tau) \exp\left(-\frac{K_{ox} + EF_b}{V_p}(t - \tau)\right) d\tau. \qquad (II)$$

Clinically meaningful information may be attached to values for $EF_b$ and $K_{ox}$ and data is present from pulmonary regions and also as parameter maps from the whole lung in the Figures.

(c) Image Registration and Application of Compartmental Model

For registration an active shape model (Cootes et al. (1995) Computer Vision and Image Understanding, 61: 38) was used to characterize normal breathing motion and then to allow the automated identification of the outline of the lung. The lung shapes were then transformed to an average shape using linear re-sampling. $T_1$ maps were calculated for air and oxygen breathing by fitting the saturation recovery images to equation III using a Levenberg-Marquardt fitting algorithm.

$$S(T_{SAT}) = A - B\exp\left(\frac{-T_{SAT}}{T_1}\right) \qquad (III)$$

To convert the dynamic signal intensity data to increase in dissolved oxygen concentration above air-breathing, the values were first converted to $T_1$ values using book-ending from $T_1$ maps (Cron et al. (1999) Magnetic Resonance in Medicine. 42 4:746-53). They were then converted to $R_1$ by inversion, the baseline air-breathing $R_1$ was subtracted, and finally the values converted to $PO_2$ (mmHg) by division by the known relaxivity constant $r_1 = 4 \times 10^{-4}$ s$^{-1}$ mmHg$^{-1}$ (Jakob et al. (2004) Magnetic Resonance in Medicine. 51: 1009-1016).

The oxygen input function was estimated from the known ratios of alveolar gas partial pressures (Martin, L (1999): All you really need to know to interpret Arterial Blood Gases. Lippincott Williams & Wilkins 2nd ed.). Alveolar $PO_2$ ($P_AO_2$) during air-breathing is typically 104 mmHg, and during 100% oxygen breathing at an atmospheric pressure of 760 mmHg it can be estimated at 673 mmHg. Hence the difference in $P_AO_2$ over air breathing can be approximated as 569 mmHg. The rate of replacement of air in the lungs is typically estimated as on average 7.5% per breath. At rest one takes an average of one breath per 5 seconds, and therefore it takes on average approximately 1 minute for all air to be replaced. This was reflected in the sloping edges of the estimated $P_AO_2$ input function (see FIG. 2a). During air replacement with 100% oxygen the lung will replace air at an unknown variable rate at the alveoli. A linear function was therefore chosen to describe the edges of the input function (in preference to an exponential or other more complex function—these options can easily be incorporated into the method) as the simplest approximation to the true form. According to varying individual lung capacity and the position within the lung, it was found that the delay time to maximum $P_AO_2$, i.e. the value of $T_{VENT}$, required optimization. Using a Levenberg-Marquardt fitting algorithm and assuming a $V_p$ fraction of 1, equation II was solved for $EF_b$ and $K_{ox}$ for averages over regions of interest at the top of each lung (see table 1). $T_{VENT}$ was a third free parameter in the fit (see FIG. 2b). Voxel-by-voxel parameter maps were also calculated (see FIG. 3). The values of $EF_b$ were converted to standard units (ml/min/ml) presuming a lung density of 0.15 g/ml near the lung periphery (Hatabu, et al. (1999). Magnetic Resonance in Medicine. 42: 1033-1038).

(d) Spirometry

The method in accordance with the first aspect of the present invention may be compared to spirometry so as to validate the diagnostic capabilities of the method in relation to lung function. Spirometry is a pulmonary function test which is commonly performed clinical situations. Currently spirometry is the main test that is used to diagnose irregular lung function. Spirometry comprises measurements taken from a subject inhaling or exhaling through a tube. A subject blows through a tube and the values of total volume exhaled in one minute ($FEV_1$) and total volume exhaled (FVC) are measured. From these values, the value of $FEV_{1\% \ PRED}$ is calculated by a function of the ratio of $FEV_1$ and FVC as compared to normal ranges known in the population. $FEV_{\% \ PRED}$ is a well known measure of the healthiness of spirometry measurements of the subject, a healthy value being greater than 0.75.

(e) Box Plots

The results shown in FIGS. 7 to 9 are shown as box plots. Box plots are known in the art. The box plot representation comprises one glyph per grouping of data, each glyph including a horizontal line at the top and bottom of the glyph, which respectively indicate the largest and smallest observed values in the group. A box shape in the glyph comprises upper, intermediate and lower horizontal lines which indicate the upper quartile range, median value and lower quartile range.

1.2 Results

Assuming an extraction fraction E of 1, the $F_b$ values given in table 1 are consistent with literature quoted values for lung perfusion (Hatabu, et al. supra). The diffusion measures obtained in $K_{ox}$ varied considerably between individuals but were mainly consistent between both lungs in each individual. The parameter $EF_b$ (FIG. 3) illustrates variation over the right lung slice area with less perfusion towards the edges and top of the lung and larger values corresponding to the main pulmonary vessels in the centre. The $K_{ox}$ parameter map shows stronger ventilation-diffusion in the centre lung but the peripheral values are more uniform to the lung edges than in the $EF_b$ map. The map of time lag $T_{VENT}$ to maximum $C_A$ shows shorter times in the centre lung and longer times at the periphery.

TABLE 1

Average compartmental model parameters obtained from left and right lungs on five individuals

| Subject | Lung | $EF_b$(ml/min/ml) | $K_{ox}$(ml/min/g) | $T_{VENT}$(s) |
|---|---|---|---|---|
| 1 | Left | 1.2677 | 4.1431 | 66 |
|   | Right | 0.8015 | 3.5409 | 68 |
| 2 | Left | 1.0762 | 2.3612 | 44 |
|   | Right | 1.3007 | 1.7382 | 42 |
| 3 | Left | 1.0106 | 17.5859 | 128 |
|   | Right | 1.1345 | 17.0257 | 75 |
| 4 | Left | 1.3892 | 5.6615 | 53 |
|   | Right | 0.7018 | 14.8614 | 61 |
| 5 | Left | 1.2639 | 0.8860 | 140 |
|   | Right | 1.0402 | 19.4285 | 83 |

1.3 Conclusions

These data present a compartmental model of oxygen delivery to the lung which allows direct assessment of pulmonary perfusion, diffusion and ventilation using OE-MRI. This may be used to detect regions of impaired ventilation, diffusion or perfusion when applied to patient groups.

This work demonstrates for the first time how lung perfusion may be estimated using OE-MRI. This technique has advantages over other methods of measuring perfusion, including ease of implementation and the lack of risk associated with the oxygen contrast agent, i.e. gadolinium based contrast agents used in DCE-MRI hold certain minimal risks of allergic reaction and elevated risks in patients with renal impairment.

In terms of understanding the delivery mechanism of oxygen, this modeling approach also provides a new means of separating the information associated with general airway health (or $T_{VENT}$, the time taken to achieve maximum $C_A$) from the rate of diffusion across the membrane ($K_{ox}$).

EXAMPLE 2

The methods described in Example 1 were applied to a group of non-smokers and a group of smokers to illustrate how the methods of the invention can be used to illustrate how lung function varies between these two groups.

These data illustrate that the method of the invention can be used to demonstrate that lung function of these two groups is different. In the smokers the $K_{ox}$ histogram is shifted to the right. This suggests a higher rate of diffusion of oxygen into the tissue which may be due to either an increased alveolar membrane permeability (consistent with other findings, Mason et al, (2001) Clinical Science, 100: 231-236) or by a greater initial gradient of oxygen concentration across the membrane in smokers due to the known lower blood oxygen in smokers, or by a combination of both. Furthermore the $EF_b$ histogram for smokers is shifted to the left and this suggests a lower blood flow from the lung tissue, which is consistent with known impeded blood circulation in smokers. Finally the ventilation time histogram is shifted to the right in the smokers, indicating that it takes longer for the inspired oxygen to reach the alveoli, due to the known airway constriction effect of smoking.

All these data are consistent with the compromised lung function that a clinician would expect to see in a smoker and demonstrate that the methods of the present invention can by utilised to obtain meaningful data relating to lung function. The difference between the two groups is predictable and illustrates that the methods may be applied to a number of prognostic or diagnostic uses.

EXAMPLE 3

In the third example, further evaluation of the compartmental model algorithm of Example 1 has been carried out using groups of smokers and non-smokers, so as to further validate the method according to the first aspect of the present invention.

3.1 Methods

The methods described in Example 1 were applied to a further group of eleven non-smokers and twelve smokers to further illustrate how the invention can be used to analyse how lung function varies between these two groups and how the unhealthy partial lung function of a subject can appear to be healthy when considered as an average of the entire lung, particularly when tested against spirometry.

(a) OE-MRI scan and Compartmental Model

The twelve smokers and eleven non-smokers each underwent an OE-MRI scan according to the method described for the first example. The data from the scan of each subject were fed into a compartmental model according to the compartmental model described above and set out in equation (II), and in example 1. Data relating to lung function such as $K_{ox}$, $EF_b$ and $T_{VENT}$ were obtained from the compartmental model, and the data were analysed. The results of the analysis are presented below.

3.2 Results

Results of fitting compartmental models in accordance with the present invention to OE-MRI data from each of the subjects is shown in a variety of forms below.

(a) Average Results for a Healthy Non-smoker

Figure 1:
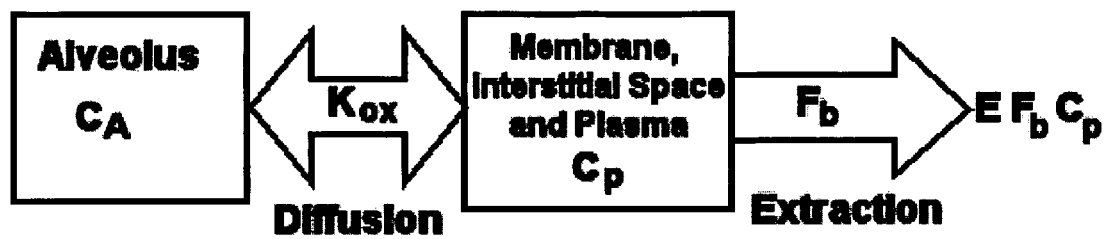
Figure 2A:
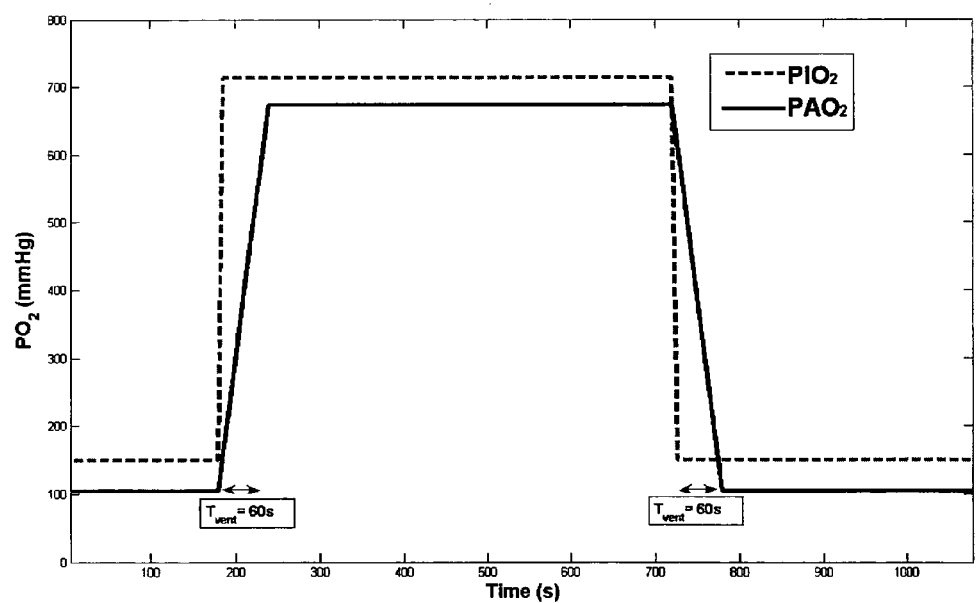
Figure 2B:
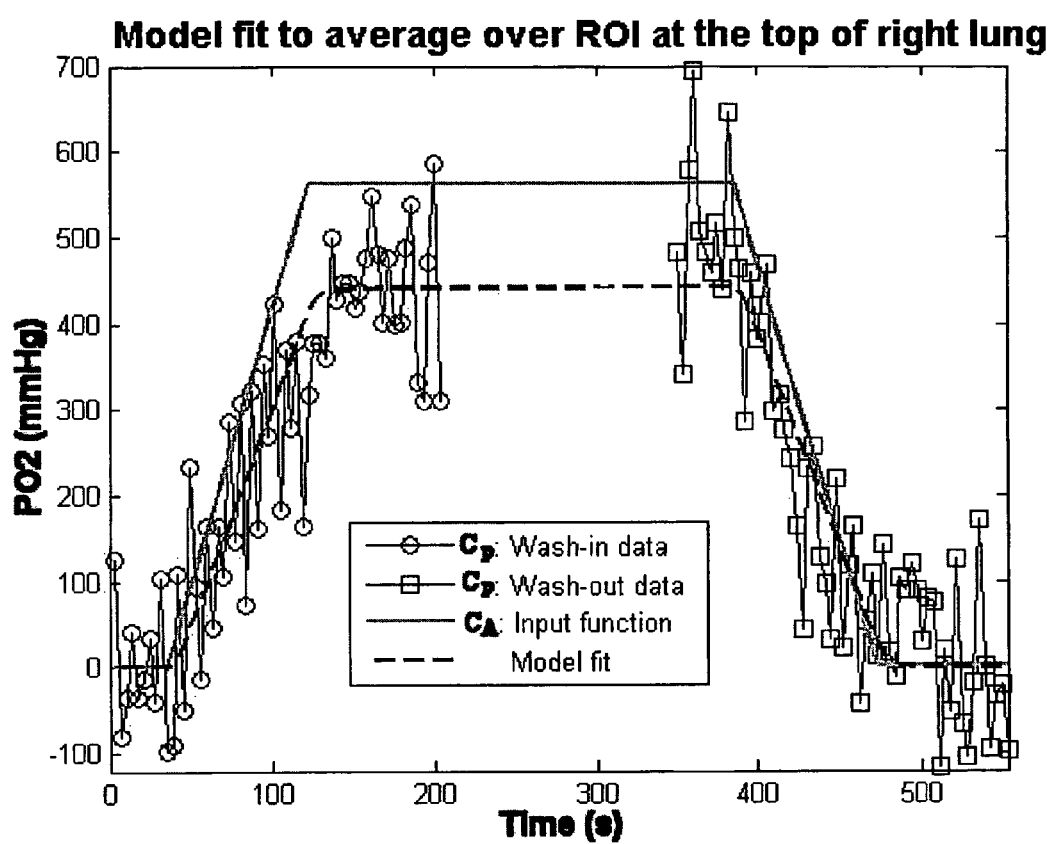
Figure 3:
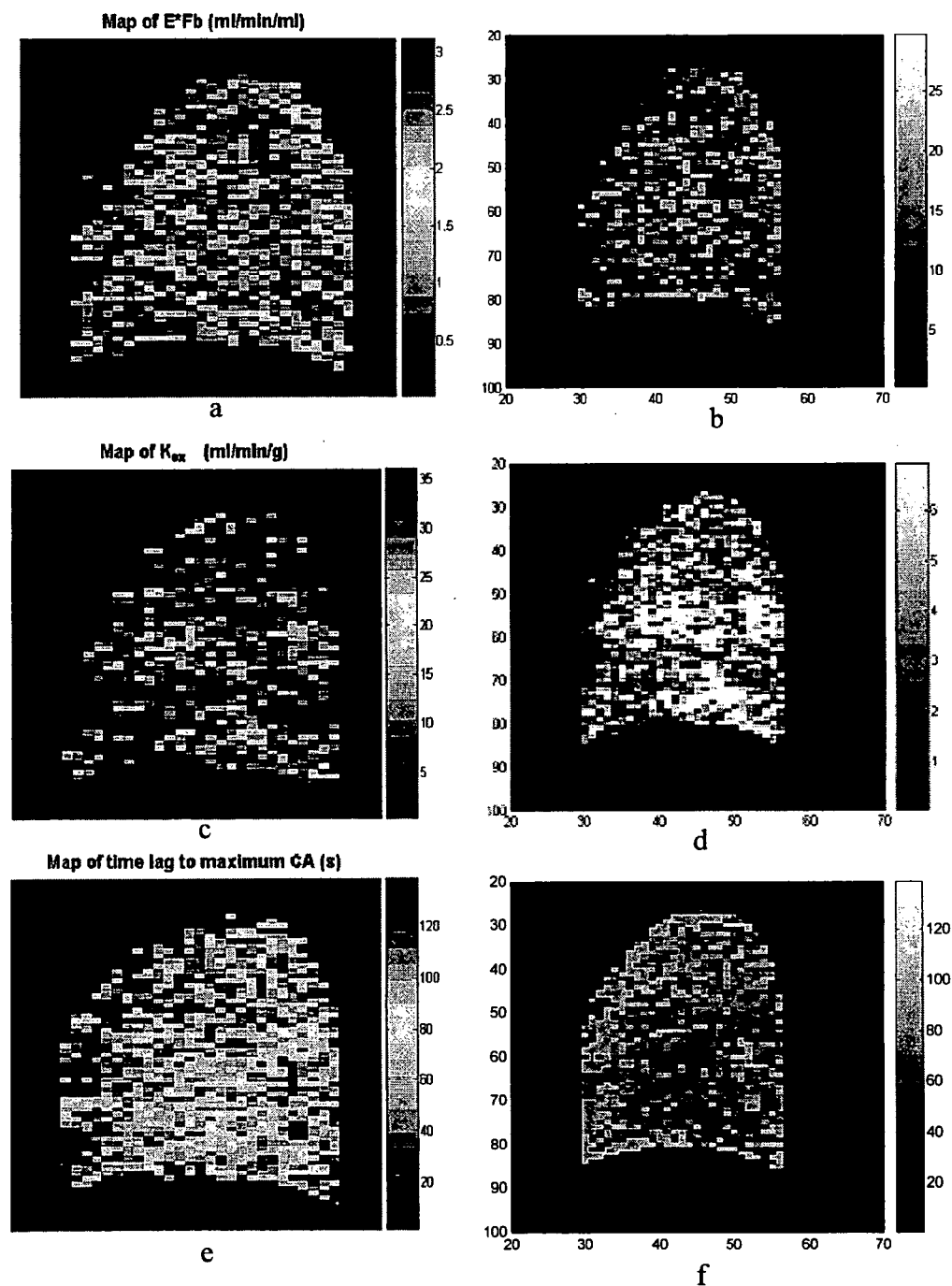
Figure 4:
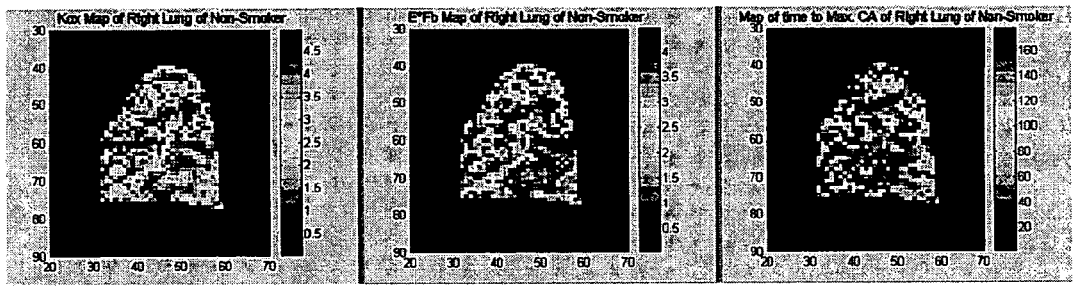
FIG. 4 represents maps and histograms of $K_{ox}$, $EF_b$ and ventilation time (respectively) for the right lung of (a) a non-smoker; and (b) a smoker.
Figure 4:
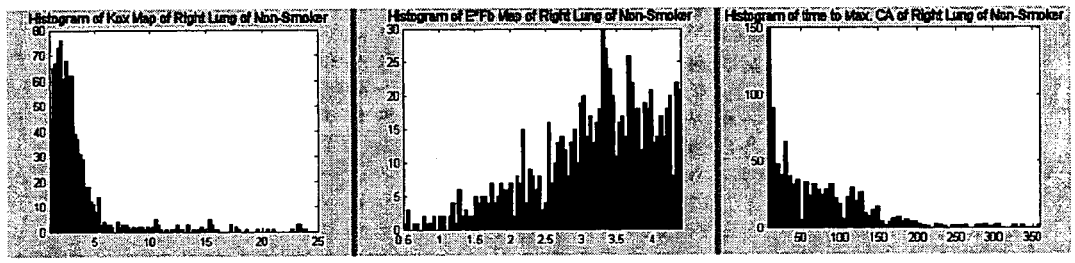
Figure 4:
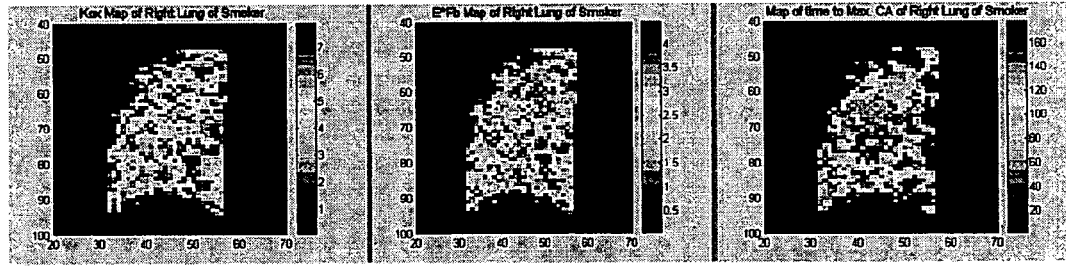
Figure 4:
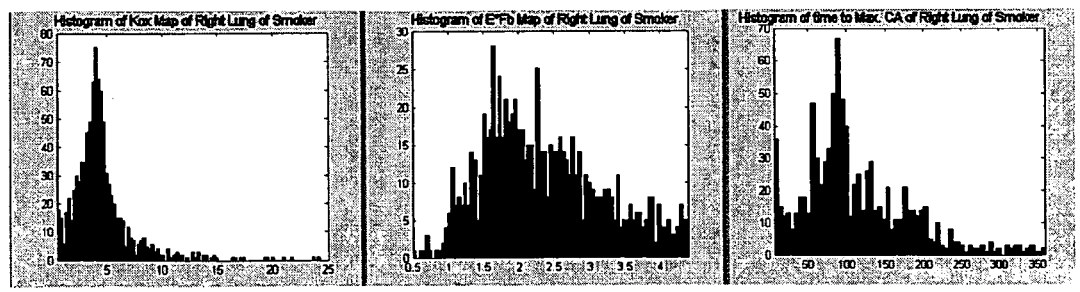
Figure 5:
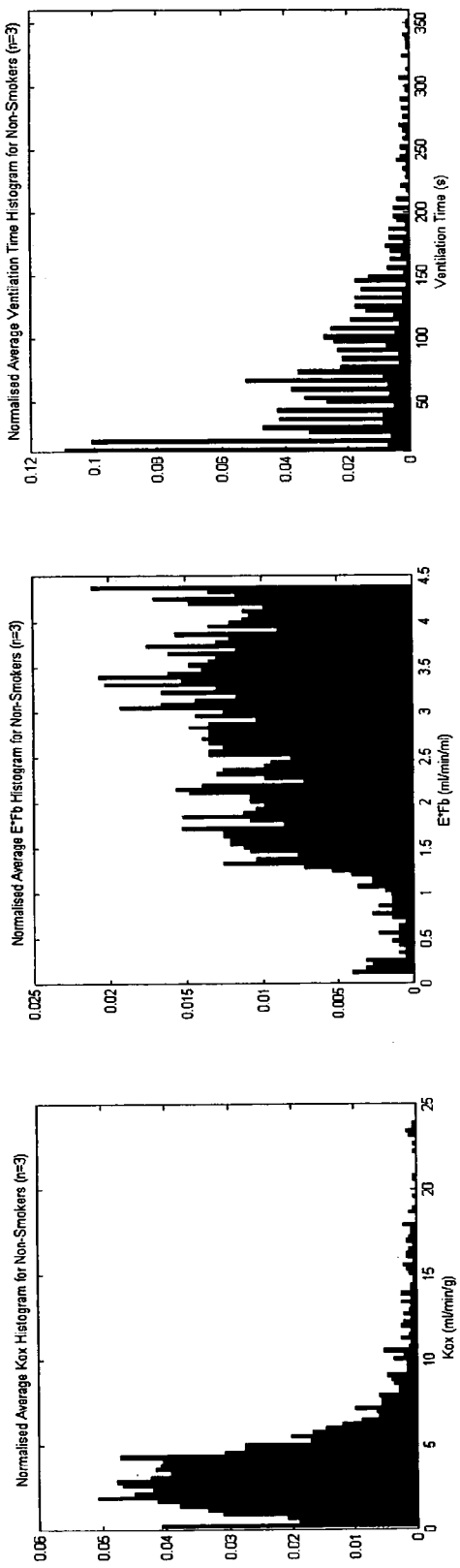
FIG. 5 represents histograms of averaged data for $K_{ox}$, $EF_b$ and ventilation time (respectively) for the right lung of (a) the non-smoker group; and (b) the smoker group.
Figure 5:
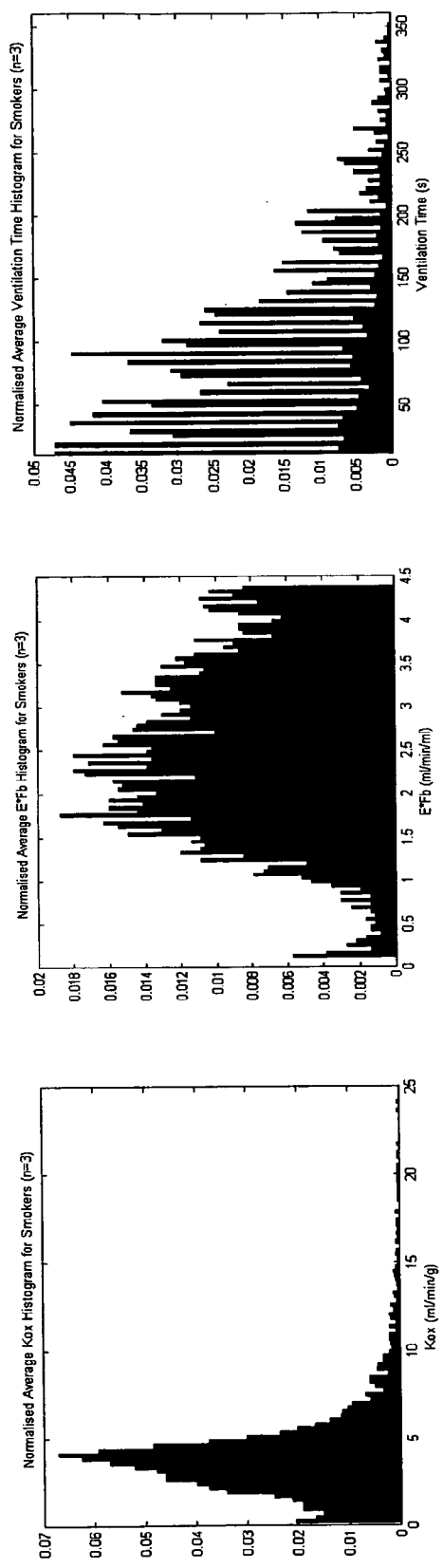
Figure 6:
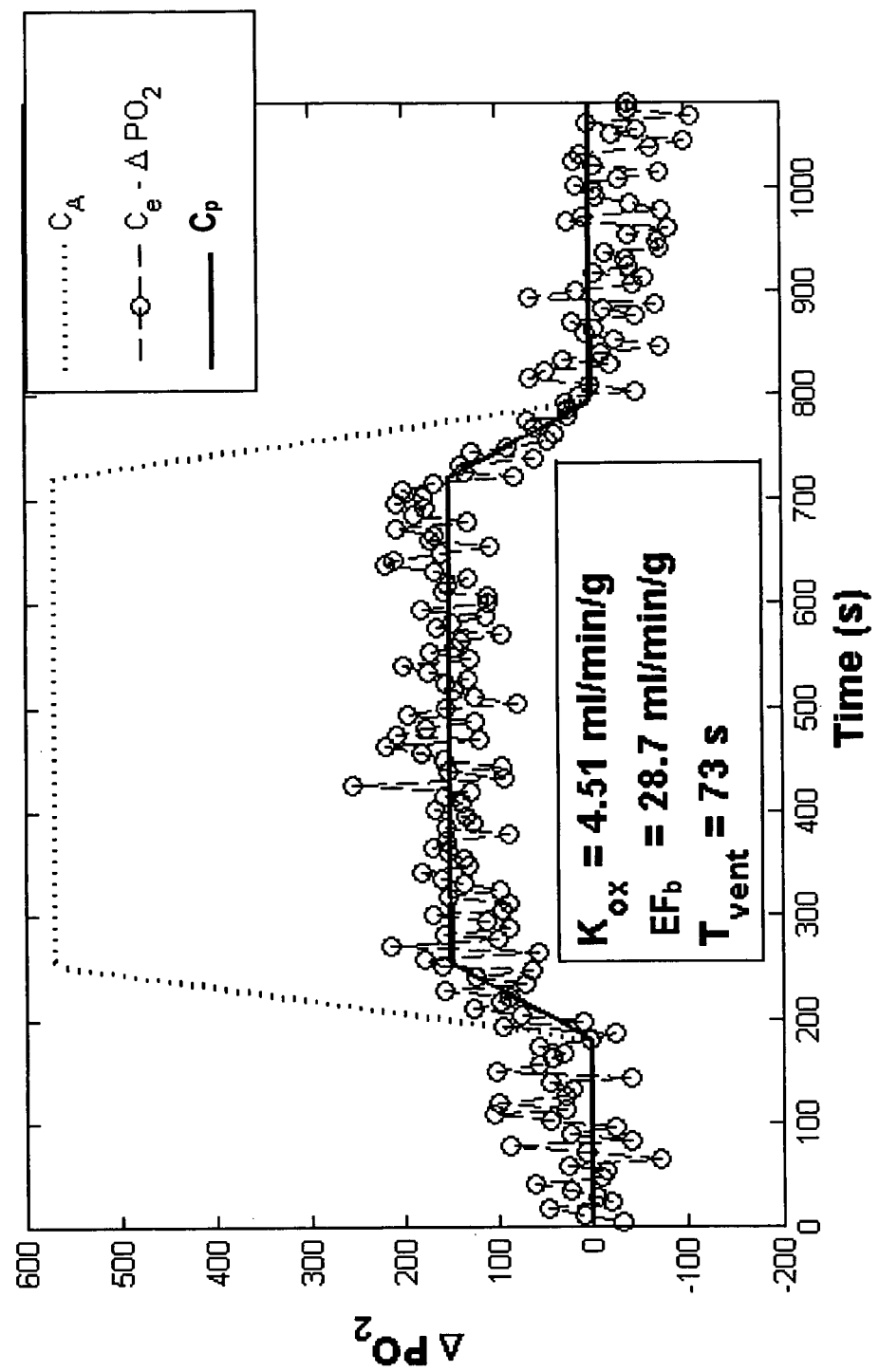

FIG. 6 shows the results of a fit of the two-compartment model to the mean right lung absorption of Oxygen (labelled $P_AO_2$) into the second compartment $C_P$ (tissues and blood) of the compartmental model for a healthy non-smoking subject breathing gas with two different partial pressures of Oxygen (labelled $P_IO_2$). As the model was fitted to mean values for the whole right lung, the resulting values of $K_{ox}$, $EF_b$ and $T_{VENT}$ represent average values for the whole right lung.

The values shown in FIG. 6 represent the difference ($\Delta PO_2$) in $PO_2$ in each compartment for two different partial pressures of oxygen breathed by the subject, the first pressure being approximate to air (21% $O_2$) and the second being pure Oxygen (100% $O_2$). At approximately 200 s, the concentration of oxygen in the gas mix being breathed by the subject was increased. As shown in FIG. 6, as the concentration of Oxygen in the first compartment $C_A$ increases, the concentration of Oxygen in the second compartment $C_p$ increases proportionally to the change in the first compartment. This continues until both compartments reach a saturation point, at which point the concentration of Oxygen in both compartments remains constant. The time taken to reach maximum Oxygen concentration in the second compartment, labelled $T_{VENT}$, for the healthy non-smoking subject is 60 s. When, at approximately 700 s, the concentration of oxygen breathed by the subject is returned to it's initial concentration at the start of the test, the concentration of Oxygen in the two compartments reduces over time to its former state.

(b) Average Results for Groups of Smokers and Non-smokers

The test described above with reference to FIG. 6 was repeated for each member of the test group, which included both smokers and non-smokers. Values of $K_{ox}$, $EF_b$ and $T_{VENT}$ were generated from compartmental model fits performed for each of the subjects. The subjects were divided into groups according to their smoking habits and general health. The smokers are divided into "All smokers" and "Smokers with >20PY", where PY is pack years, which is the number of packs of cigarettes smoked per day by the number of years for which that number of packs have been smoked. A person of 20 PY may, for example, have smoked one pack per day for twenty years, or perhaps two packs per day for ten years. The non-smokers are divided into "healthy" non-smokers and "All non-smokers". Healthy smokers were defined as those with a healthy spirometry test, 0 PY and no regular exposure to passive smoke. The results for each group are shown in the box-plots depicted in FIGS. 7 to 9.

Figure 7:
Figure 8:

FIG. 7 shows a box plot of comparative results for $K_{ox}$ between the group of twelve smokers and eleven non-smokers. It is clear from FIG. 7 that the median values of $K_{ox}$ between smokers and non-smokers are significantly different. This shows that it is possible to discriminate between smokers and non-smokers merely by computing an average $K_{ox}$ value for each subject. Since the value of $K_{ox}$ for a subject is indicative of the rate of diffusion of Oxygen across the alveolar membrane. FIG. 8 shows comparative results for values of $EF_b$ which were extracted from the compartmental model for each of the groups of subjects. As described above, $EF_b$ is a measure of the rate at which oxygen is removed from the lung tissues by the blood. As the rate at which Oxygen is removed from the lung tissues for transport around the body is critical to the healthy respiratory function of the subject, this value is an important measure of damage to the respiratory system. It is clear from these results that $EF_b$ in healthy, and unhealthy, non-smoking subjects is higher than for either of the smoking groups. This reduced respiratory function is an important factor in the health of the subjects and could not be directly detected by methods such as $^{129}$Xe imaging because the data produced by such techniques would relate to the rate at which $^{129}$Xe, rather than Oxygen, is removed from the lung tissues.

Figure 9:
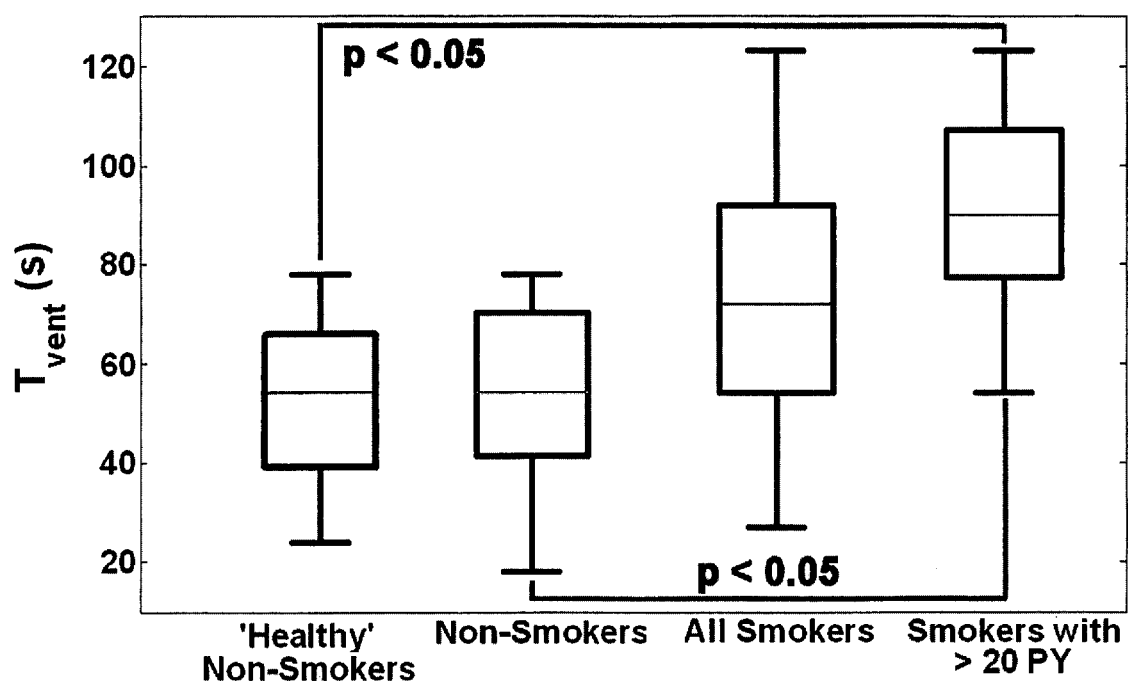

FIG. 9 shows comparative results for the wash in and wash out values $T_{VENT}$ between the groups of subjects. The time taken to reach maximum Oxygen concentration in the compartments ($T_{VENT}$) of the compartmental model is indicative of the efficiency of each breath of an individual in clearing out old gas from the lungs and introducing new gas into the lungs. The value of $T_{VENT}$ is also a good indication of the time taken for new air in the lungs to be dissolved into the lung tissues. It is clear from these results that the non-smoking groups generally have a much lower value of $T_{VENT}$ than the smoking groups. This again indicates reduced lung function in the patient.

For each of the measures shown in FIGS. 7, 8 and 9 it is clear that the values which can be extracted from the compartmental model of the present invention are capable of measuring a detectable difference between various aspects of the lung function of smokers and non-smokers. More particularly, the values are capable of showing differences between each of the four groups shown in FIGS. 7, 8 and 9.

(c) Exemplary Lung Function Maps

Figure 10:
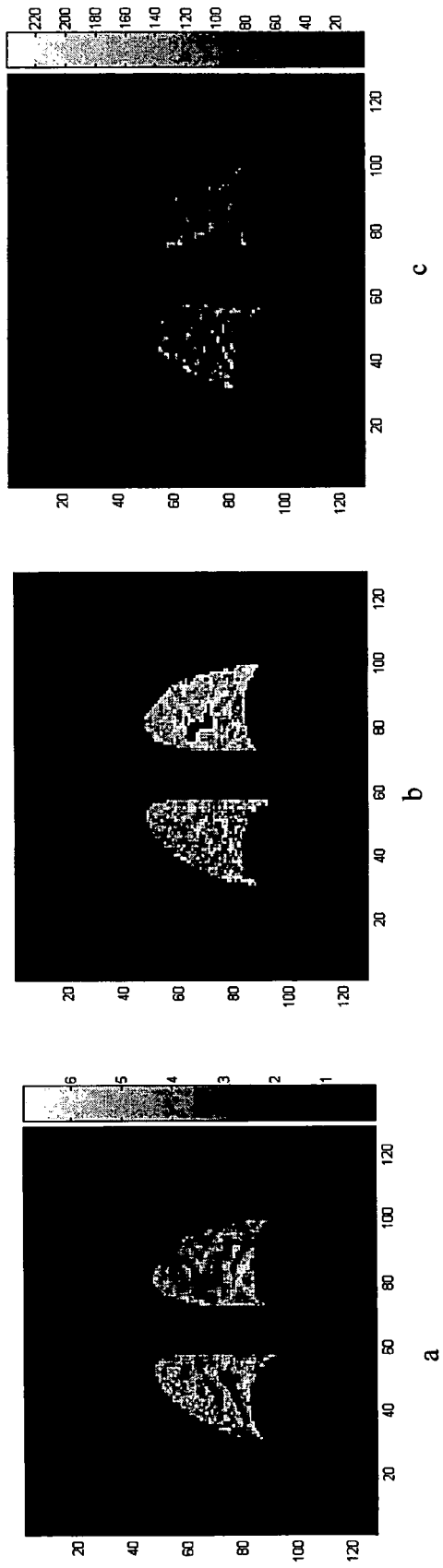
Figure 11:
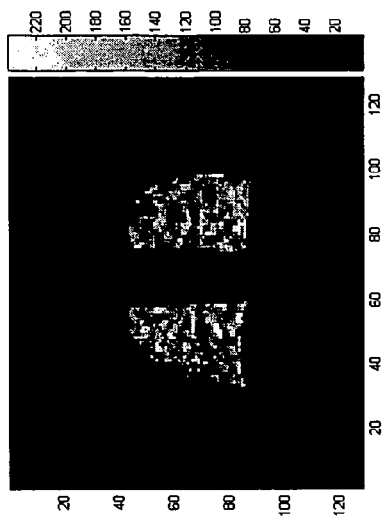
Figure 11:
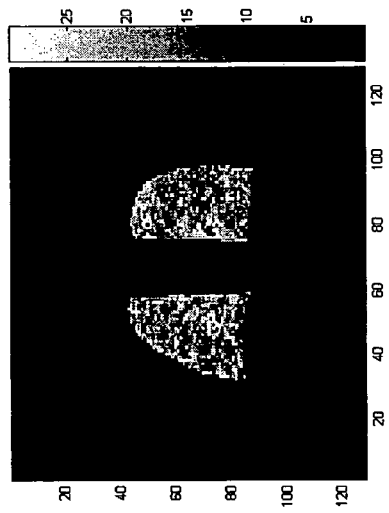
Figure 11:
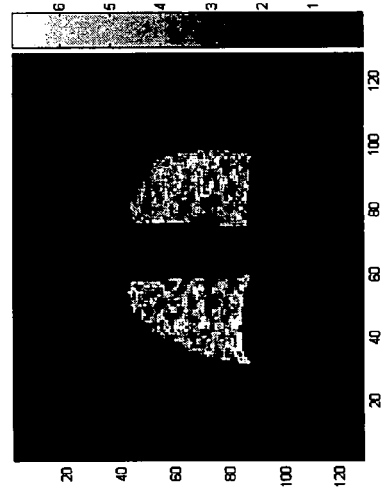
Figure 12:
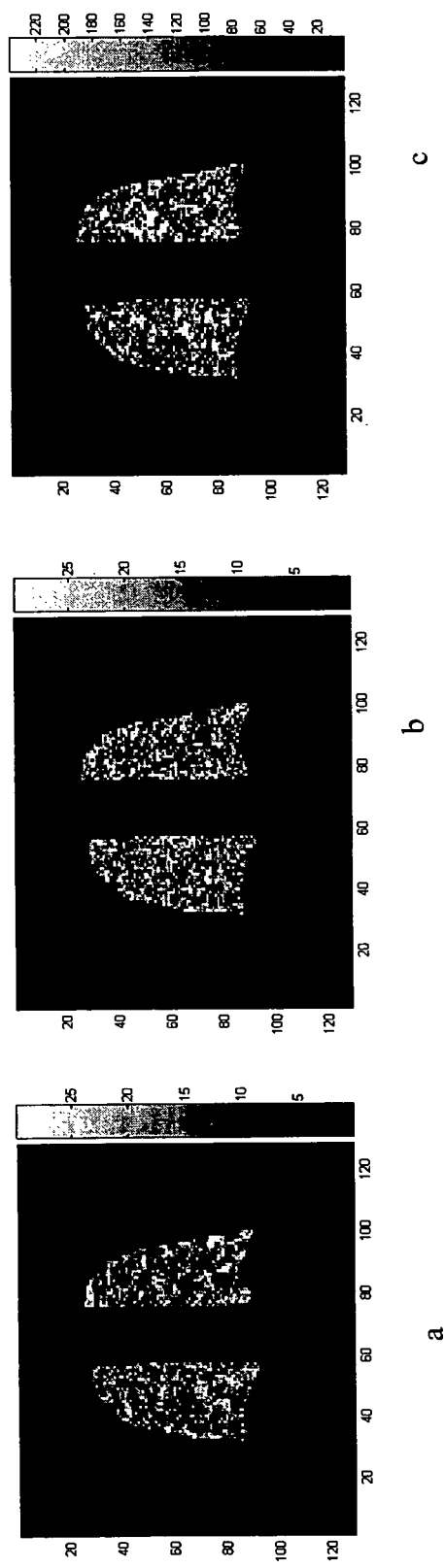

The results presented in section (b) above were generated as average values across the whole right lung of each individual. However, a compartmental model in accordance with the present invention is capable not merely of generating broad measures across the entire lung, but of generating lung parameter maps which show individual values of measures such as $K_{ox}$, $EF_b$ and $T_{VENT}$ for each voxel in the data generated by the OE-MRI which contains lung tissue or blood. The following results, shown in FIGS. 10, 11 and 12, are examples of such lung parameter maps which were generated for subjects who took part in the testing described in the present example. In order to compare the results of the compartmental model of the present invention with an existing diagnostic method, the subjects also underwent spirometry tests which determined values of $FEV_{\% PRED}$ for each of the subjects.

FIGS. 10a, 10b and 10c show lung parameter maps respectively for $K_{ox}$, $EF_b$ and $T_{VENT}$ for a subject who is a healthy, non-smoking female, aged 23 years old. Bright pixels in the map indicate high values for each measurement, while dark pixels in the map indicate lower values. The subject had a spirometry value of $FEV_{\% PRED}=93\%$, which indicates that she has healthy lung function. The median results, which contributed to the statistical results shown in FIGS. 7 to 9, which were extracted from the compartment model for this subject are:

Median $K_{ox}$=3.19 ml/min/g

Median $EF_b$=19.4 ml/min/g

Median $T_{VENT}$=24 s

The grey levels in the lung function map for $K_{ox}$, shown in FIG. 12a, are uniform across each lung, which indicates that the difference in the rate of diffusion across alveolar membranes between different areas of the lung are small. Similar results are shown in FIG. 12b, which shows that the rate at which dissolved oxygen is removed from the lung tissues is uniformly high across each lung. Finally, FIG. 12c shows that the wash in and wash out time for each lung is generally equally low across the extent of the lungs, although some areas of high $T_{VENT}$ are evident in the lung shown on the right. This shows that the entire area of this subject's lungs is functioning well and contributing to respiration in the subject. Large, distinct, black regions are visible in each lung of each image, but these correspond to large areas of bronchus, or airway, which transports air into and out of each lung. These areas have low values of $K_{ox}$, $EF_b$ and $T_{VENT}$ as there is no second compartment measurement due to the lack of tissue and blood in the area.

FIGS. 11a, 11b and 11c show image results respectively for $K_{ox}$, $EF_b$ and $T_{VENT}$ for a second subject who is an apparently healthy, smoking female, aged 54 years old. The subject had a spirometry measurement of $FEV_{\% PRED}=92\%$, which indicates lung function which is within the healthy range. The median results which were extracted from the compartment model for this subject, and which contributed to the statistical results shown in FIGS. 7 to 9, are:

Median $K_{ox}$=3.7 ml/min/g

Median $EF_b$=16.6 ml/min/g

Median $T_{VENT}$=90 s

The median values for $K_{ox}$ and $EF_b$ for the subject are lower than those for the healthy non-smoking subject, which indicates slightly reduced overall lung function for this subject. It can be seen that the grey levels in the lung parameter maps of $K_{ox}$ and $EF_b$ shown in FIGS. 11a and 11b differ from the images shown in FIGS. 10a and 10b in that there are small darkened regions throughout the lungs. This indicates that rates have been reduced for diffusion of Oxygen across the alveolar membrane and for removal of Oxygen from the lung tissues by the blood. The two images alone show reduced lung function in the subject in many areas of the lungs. In addition to FIGS. 11a and 11b, 11c shows the time taken for each area of the lungs to reach maximum concentration of Oxygen ($T_{VENT}$). When compared to the lung parameter map for $T_{VENT}$ in the healthy, non-smoking subject, shown in FIG. 10c, the lung parameter map of $T_{VENT}$ for the apparently healthy smoking subject, shown in FIG. 11c, is clearly brighter in many areas. This indicates that the time to reach maximum saturation of Oxygen for the subject is longer, and that therefore lung function is not as efficient as for the healthy non-smoker.

This means that although this subject showed normal results in a standard spirometry test, they in fact have decreased lung function in some areas in their lungs. It would not be possible to directly diagnose this irregularity of function by any other means. This indicates that the diagnostic capabilities of the method of the present invention are able to detect lung abnormalities in circumstances where spirometry shown normal performance, a presents a significant advantage over previous methods.

FIGS. 12a, 12b and 12c show lung parameter maps respectively for $K_{ox}$, $EF_b$ and $T_{VENT}$ for an unhealthy, smoking male subject aged 57 years old. The subject has been diagnosed with type IIB chronic obstructive pulmonary disease (COPD). The smoker has a $FEV_{\% PRED}$=39%, which indicates substantially reduced lung function. The median results of the subject for his entire right lung, which were extracted from the compartment model are:

Median $K_{ox}$=3.34 ml/min/g

Median $EF_b$=16.9 ml/min/g

Median $T_{VENT}$=123 s

It is clear from the median values for $K_{ox}$, $EF_b$ and $T_{VENT}$, particularly the value of $T_{VENT}$, that lung function in the subject is reduced in comparison to either of the two subjects whose results are shown in FIGS. 10 and 11. The black regions in the $K_{ox}$ and $EF_b$ lung parameter maps, shown in FIGS. 12a and 12b, indicate that the lung tissue in those regions is not functioning. The white regions in the $T_{VENT}$ lung parameter map indicate that those lung regions are taking a very long time to reach a maximum concentration of oxygen. Completely black regions in FIG. 12c indicate that the area of the lung reaches a maximum concentration of oxygen very quickly, although it is clear from the low values of FIGS. 12a and 12b that the maximum concentration of oxygen is substantially lower for this subject than for the subjects whose results are shown in those figures.

(d) Correlation with Independent Measures in DCE-MRI

The inventors compared the compartmental model algorithm of the present example with a measurement of the product of permeability and surface area (PS) of the lungs of the same subjects, which was produced by standard DCE-MRI. It should be noted that, although the measurement of PS is the current standard for assessment of the permeability of the lungs, it is a measurement of the permeability of the lung capillary walls to a non-oxygen contrast agent and not to oxygen itself. Therefore, any measurements of lung permeability to oxygen from DCE-MRI are indirect measurements which are calculated from the direct measurements of contrast. In this case the contrast agent used in the DCE-MRI was a gadolinium-based low molecular weight agent.

Figure 13:
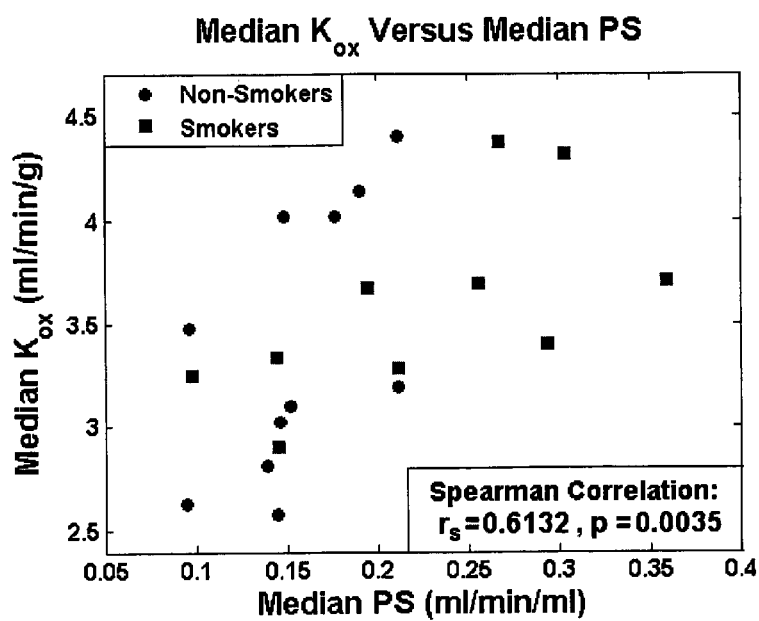
Figure 14:
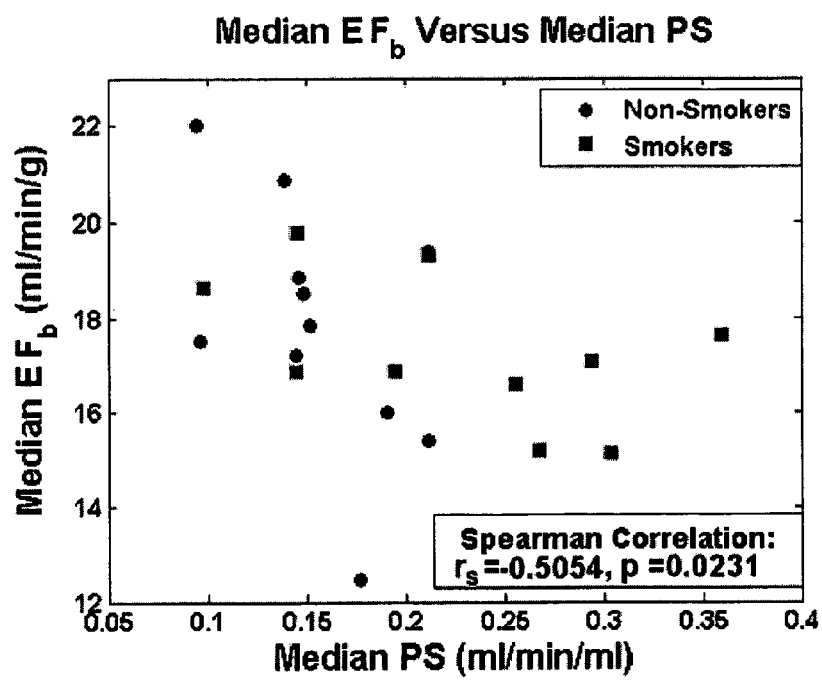

FIG. 13 shows a correlation between the $K_{ox}$ measurement of the present invention and the PS (permeability×surface area) measurement of DCE-MRI. FIG. 14 shows a correlation between the $EF_b$ measurement of the present invention and the PS measurement of DCE-MRI. This indicates that a method according to the present invention may be used in place of DCE-MRI, in order to ameliorate the many problems associated with creating, storing and transporting contrast agents and with introducing such contrast agents into in vivo subjects.

3.3 Conclusions

This example has shown that a method in accordance with the present invention applied to OE-MRI image data of smokers and non-smokers is capable of differentiating between the local function of the lungs of smokers and non-smokers, and in some cases is capable of diagnosing a decrease in local lung function when a global assessment of lung function, via spirometry, appears to be clinically normal. It has been shown by comparison with DCE-MRI that a method according to the present invention may be used in addition to, or in place of, DCE-MRI for the diagnosis of pathological lung function.

EXAMPLE 4

In this example, the inventors implemented a compartmental model algorithm in accordance with an aspect of the present invention. The algorithm was implemented as software in Matlab script. The inventors packaged the Matlab script, which implements the compartmental model algorithm, for distribution on a compact disc.

The compact disc containing the software was given in confidence to an operative who was in possession of a 1.5 T Philips Gyroscan NT Intera MR scanner. The operative used the scanner, together with Oxygen breathing apparatus widely available in medical environments, to performed an OE-MRI scan on a human patient according to the method described in the first example. The operative then used the software on the compact disc to analyse the data generated by the OE-MRI scan of the patient so as to characterise the patient's lung function, in accordance with an aspect of the present invention.

The compartmental model generated values indicative of the patient's lung function, including $K_{ox}$, $EF_b$ and $T_{VENT}$. The software displayed the values generated by the compartmental model in a number of ways, including as a series of graphs and lung parameter maps. The data values, the graphs and the lung parameter maps were used by a medical professional to analyse the lung function of the patient and diagnose illness in the patient. The sensitivity of the model to the function of relatively small areas of the patient's lungs allowed the medical professional to diagnose local areas of low lung function within the lungs and to target therapy accordingly. The use of OE-MRI to generate the data which was input into the compartmental modelling software was particularly new and interesting in that the medical professional was able to directly analyse the function of the lung in relation to Oxygen ventilation, diffusion and perfusion. This direct analysis has not been possible before the present invention.

The invention claimed is:

1. A method of characterising lung function in a subject in need of such characterisation comprising:
   performing, with an imaging system having a computer and a processor, an Oxygen-Enhanced Magnetic Resonance Imaging (OE-MRI) technique, on a voxel defined within a lung space of interest,
   generating image data, with the imaging system, over a time period during which the subject inhales gases with at least two different partial pressures of oxygen; and
   applying a compartmental model algorithm, with the processor, to the image data generated for the voxel over said time period to measure rates at which oxygen was removed from an alveoli gaseous space into a fluid of an alveolar membrane, interstitial spaces and alveolar capillaries and removed from the alveolar capillaries when taken into the body via a blood stream to provide information on ventilation, diffusion across the alveolar membrane and perfusion of a lung.

2. The method of claim 1, further comprising dividing the lung space into a matrix of voxels and generating OE-MRI data for each voxel.

3. The method of claim 2, wherein the OE-MRI data is generated while the subject first inhales a first gas with a partial pressure of oxygen between 0% and 35% oxygen; then breathes a second gas with a partial pressure of oxygen between 45% and 100% oxygen; and finally inhales the first gas again.

4. The method of claim 3 wherein the first gas is air and the second gas is 100% oxygen.

5. The method according to claim 1, further comprising applying techniques to improve image registration to ensure that the imaging technique is conducted on the same voxel over time.

6. The method according to claim 1 wherein the compartmental model algorithm is a two-compartment model based on physiological parameters for rate of ventilation of the lungs, oxygen diffusion across alveoli and pulmonary blood flow.

7. The method according to claim 6, further comprising calculating, with the compartmental model algorithm, combined oxygen concentration of a second compartment comprising the alveolus membrane, interstitial space between the membrane and pulmonary capillaries and the plasma within the capillaries ($C_p$).

8. The method according to claim 6, further comprising calculating, with the compartmental model algorithm, fractional volume of blood plasma and tissue water per MRI visible tissue ($V_p$)).

9. The method according to claim 6, further comprising calculating, with the compartmental model algorithm, diffusing capacity of the alveolar membrane ($K_{ox}$).

10. The method according to claim 6, further comprising calculating, with the compartmental model algorithm, E, the extraction fraction of oxygen from the tissue water and capillaries, and $F_b$ the rate of blood flow in the capillaries.

11. The method according to claim 6, further comprising calculating, with the compartmental model algorithm, time to achieve maximum concentration of oxygen (CA) in the alveolus space, a parameter of the oxygen input function CA.

12. The method according to claim 6 wherein the algorithm is:

$$C_p = \frac{K_{ox}}{V_p} \int C_A(\tau) \exp\left(-\frac{K_{ox} + EF_b}{V_p}(t - \tau)\right) d\tau. \quad \text{(II)}$$

as defined herein.

13. The method according to claim 1, wherein the method evaluates lung function in humans or animals for either diagnostic or prognostic purposes or for therapeutic development.

14. An apparatus for generating and characterizing data concerning lung function in a subject, the apparatus comprising:
   a computer in communication with the apparatus;
   a memory storing processor readable instructions; and
   a processor configured to read and execute instructions stored in said memory, the processor being operable to
      perform an Oxygen-Enhanced Magnetic Resonance Imaging (OE-MRI) technique on a voxel defined within a lung space of interest;
      generate image data over a time period during which the subject inhales gases with at least two different partial pressures of oxygen, and
      apply a compartmental model algorithm to the image data generated for the voxel over said time period to measure rates at which oxygen was removed from an alveoli gaseous space into a fluid of an alveolar membrane, interstitial spaces and alveolar capillaries and removed from the alveolar capillaries when taken into the body via a blood stream to provide information on ventilation, diffusion across the alveolar membrane and perfusion of a lung.

15. A non-transitory computer readable medium comprising computer readable program code for characterizing data concerning lung function in a subject, the program code configured to cause a computer to
   perform an Oxygen-Enhanced Magnetic Resonance Imaging (OE-MRI) technique on a voxel defined within a lung space of interest;
   generate image data over a time period during which the subject inhales gases with at least two different partial pressures of oxygen, and
   apply a compartmental model algorithm to the image data generated for the voxel over said time period to measure rates at which oxygen was removed from an alveoli gaseous space into a fluid of an alveolar membrane, interstitial spaces and alveolar capillaries and removed from the alveolar capillaries when taken into the body via a blood stream to provide information on ventilation, diffusion across the alveolar membrane and perfusion of a lung.

* * * * *